United States Patent
Dellinger et al.

(10) Patent No.: US 10,280,190 B2
(45) Date of Patent: May 7, 2019

(54) NICOTINIC ACID RIBOSIDE OR NICOTINAMIDE RIBOSIDE COMPOSITIONS, REDUCED DERIVATIVES THEREOF, AND THE USE THEREOF TO ENHANCE SKIN PERMEATION IN TREATING SKIN CONDITIONS

(71) Applicants: ChromaDex Inc., Irvine, CA (US); The Queen's University of Belfast, Belfast (GB)

(72) Inventors: Ryan Dellinger, Azusa, CA (US); Marie Eugenie Migaud, Lurgan (GB); Philip Redpath, Portadown (GB); Troy Rhonemus, Mission Viejo, CA (US); Richard Cunningham, Portadown (GB)

(73) Assignees: ChromaDex, Inc., Irvine, CA (US); The Queen's University of Belfast, Belfast (IE)

( * ) Notice: Subject to any disclaimer, the term of this patent is extended or adjusted under 35 U.S.C. 154(b) by 76 days.

(21) Appl. No.: 15/072,121

(22) Filed: Mar. 16, 2016

(65) Prior Publication Data

US 2016/0272668 A1  Sep. 22, 2016

Related U.S. Application Data

(60) Provisional application No. 62/133,845, filed on Mar. 16, 2015.

(51) Int. Cl.
| | |
|---|---|
| C07H 19/048 | (2006.01) |
| A61Q 19/08 | (2006.01) |
| A61Q 19/00 | (2006.01) |
| A61K 8/67 | (2006.01) |

(52) U.S. Cl.
CPC ........... *C07H 19/048* (2013.01); *A61K 8/675* (2013.01); *A61Q 19/00* (2013.01); *A61Q 19/08* (2013.01); *A61Q 19/004* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 7,776,326 B2 | 8/2010 | Milbrandt et al. | |
| 8,106,184 B2 | 1/2012 | Sauve et al. | |
| 8,383,086 B2 | 2/2013 | Brenner | |
| 2006/0229265 A1 | 10/2006 | Milburn et al. | |
| 2012/0172584 A1* | 7/2012 | Sauve | C07H 19/048 536/28.1 |
| 2015/0056274 A1 | 2/2015 | Zemel et al. | |

FOREIGN PATENT DOCUMENTS

| | | |
|---|---|---|
| WO | 2015/014722 A1 | 2/2015 |
| WO | 2015/066382 A1 | 5/2015 |
| WO | WO2015/186114 | * 10/2015 |
| WO | 2015/186114 A1 | 12/2015 |

OTHER PUBLICATIONS

Davies et al., Nucleosides & Nucleotides, 14(3-5), 1995, pp. 311-312.*
Tietze to al., Angewandte Chemie, 1985, 97(2), pp. 135-136.*
Berge, S. M., et al., Pharmaceutical Salts. J Pharm Sci. Jan. 1977;66(1):1-19.
Paudel, K. S., et al., Challenges and opportunities in dermal/transdermal delivery. Ther Deily. Jul. 2010;1(1):109-31.
Thong, HY, et al., Percutaneous penetration enhancers: an overview. Skin Pharmacol Physiol. 2007;20(6):272-82. Abstract Only.

* cited by examiner

*Primary Examiner* — Traviss C McIntosh, III
(74) *Attorney, Agent, or Firm* — Amin Talati Upadhye LLP; Adam D. Sussman; George M. Carrera, Jr.

(57) ABSTRACT

Derivatives of nicotinic acid riboside (NAR), nicotinamide riboside (NR), and reduced NAR and NR, including 1-(2', 3',5'-triacetyl-beta-D-ribofuranosyl)-1,4-dihydronicotinic acid (4a), and compositions containing the same and/or reduced derivative forms of nicotinamide riboside including 1-(2',3',5'-triacetyl-beta-D-ribofuranosyl)-1,4-nicotinamide (2), are provided for use in the care of treatment of skin and skin conditions. In some embodiments, the invention relates to pharmaceutical compositions and cosmetic compositions containing one or more NR, NAR, NRH, or NARH derivatives, or prodrugs or salts thereof. In further embodiments, the invention relates to methods of using one or more NR, NAR, NRH, or NARH derivatives, or prodrugs, solvates, or salts thereof, to promote the increase of intracellular levels of nicotinamide adenine dinucleotide (NAD+) in cells and tissues for improving cell and tissue survival and overall cell and tissue health.

26 Claims, 6 Drawing Sheets

NICOTINIC ACID RIBOSIDE OR NICOTINAMIDE RIBOSIDE COMPOSITIONS, REDUCED DERIVATIVES THEREOF, AND THE USE THEREOF TO ENHANCE SKIN PERMEATION IN TREATING SKIN CONDITIONS

This application claims the benefit of U.S. Provisional Application No. 62/133,845, filed on Mar. 16, 2015. The disclosure of this prior application is incorporated herein by reference in its entirety for all purposes.

TECHNICAL FIELD

In certain embodiments, the invention relates to pharmaceutical compositions and cosmetic compositions containing: derivatives of nicotinamide riboside ("NR"), including 1-(2',3',5'-triacetyl-beta-D-ribofuranosyl)-nicotinamide ("NR triacetate" or "NRTA"); derivatives of a reduced form of nicotinamide riboside ("NRH"), including 1-(2',3',5'-triacetyl-beta-D-ribofuranosyl)-1,4-dihydronicotinamide ("NRH triacetate" or "NRH-TA"); derivatives of nicotinic acid riboside ("NAR"), including 1-(2',3',5'-triacetyl-beta-D-ribofuranosyl)-nicotinic acid ("NAR triacetate" or "NARTA); or derivatives of a reduced form of nicotinic acid riboside ("NARH"), including 1-(2',3',5'-triacetyl-beta-D-ribofuranosyl)-1,4-dihydronicotinic acid ("NARH triacetate" or "NARH-TA"). In further embodiments, the invention relates to methods of using the compounds above to promote the increase of intracellular levels of nicotinamide adenine dinucleotide ("NAD+") in cells and tissues for improving cell and tissue survival and overall cell and tissue health.

BACKGROUND

Enzymes that use NAD+ play a part in the DNA repair process. Specifically, the poly(ADP-ribose) polymerases ("PARPs"), particularly PARP-1, are activated by DNA strand breaks and affect DNA repair. The PARPs consume NAD+ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular NAD+, leading to cellular necrosis. The apparent sensitivity of NAD+ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of NAD+ metabolism in genotoxicity can be partially effective in improving cell survival but that other players that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that NAD+ metabolism is in important player in cell stress response pathways. For example, upregulation of NAD+ metabolism, via nicotinamide/nicotinic acid mononucleotide overexpression, has been shown to protect against neuron axonal degeneration, and nicotinamide, used pharmacologically, has been recently shown to provide neuron protection in a model of fetal alcohol syndrome and fetal ischemia. Such protective effects could be attributable to upregulated NAD+ biosynthesis, which increases the available NAD+ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

Examples of cell and tissue protection linked to NAD+ and sirtuins include the finding that SIRT1 is required for neuroprotection associated with trauma and genotoxicity. SIRT1 can also decrease microglia-dependent toxicity of amyloid-beta through reduced NFKB signaling. SIRT1 and increased NAD+ concentrations provide neuroprotection in a model of Alzheimer's disease. Sirtuins are NAD+-dependent enzymes that have protein deacetylase and ADP-ribosyltransferase activities that upregulate stress response pathways. Evidence indicates that SIRT1 is upregulated by calorie restriction and in humans could provide cells with protection against apoptosis via downregulation of p53 and Ku70 functions. In addition, SIRT1 upregulates FOXO-dependent transcription of proteins involved in reactive oxygen species ("ROS") detoxification, such as MnSOD. The sirtuin SIRT6 has been shown to participate in DNA repair pathways and to help maintain genome stability. With respect to nicotinyl ribosides including nicotinamide riboside, various uses have been proposed as in U.S. Pat. Nos. 8,106,184 and 8,383,086, herein incorporated by reference.

Therefore, it is hypothesized that a cytoprotective agent, including derivatives and reduced forms of NR and NAR (namely "NRH" and "NARH") for use in treating several human skin disorders will be effective at treating or preventing oxidative damage and in helping to maintain healthy human skin.

If new NR, NAR, NRH, and NARH derivatives could be found, and a way could be found to use NR, NAR, NRH, and NARH, and known or novel derivatives or salts thereof, in a topical skin care composition in the maintenance of healthy human skin, this would represent a useful contribution to the art. Furthermore, if a way could be found to use NR, NAR, NRH, and NARH, and known or novel derivatives or salts thereof, in a cosmetic or cosmeceutical composition in the maintenance of healthy human skin, this would also represent a useful contribution to the art.

SUMMARY

NR, NAR, NRH, and NARH derivatives, prodrugs, or salts thereof were designed to facilitate delivery of NR or NAR (or their reduced forms NRH and NARH) into the skin (of a mammal, human, etc.) using topical administration. Specifically, these derivatives will have better efficacy in the skin due to their more effective delivery due to increased lipophilicity. More effective delivery of these NAD precursors will enhance their ability to be used in the care or treatment of skin and skin conditions. In some embodiments, the invention relates to NR, NAR, NRH, and NARH derivatives, prodrugs, solvates, or salts thereof. In further embodiments, the invention relates to pharmaceutical compositions and cosmetic compositions containing NR, NAR, NRH, and NARH derivatives, prodrugs, solvates, or salts thereof. In further embodiments, the invention relates to methods of using NR, NAR, NRH, and NARH derivatives, prodrugs, or salts thereof to promote the increase of intracellular levels of nicotinamide adenine dinucleotide (NAD+) in cells and tissues for improving cell and tissue survival and overall cell and tissue health. In further embodiments, the invention relates to derivatives of other established NAD+ precursor molecules ("NMN," "NaMN," and their reduced forms) that would facilitate enhanced delivery of these molecules to the skin.

A cytoprotective method is provided for treating or preventing oxidative damage in the skin of an individual comprising topically administering to the individual in need of such treatment a therapeutically effective amount of a NR, NAR, NRH, and/or NARH derivative, prodrug, solvate, or salt thereof, including a compound selected from 1-(2',3',5'-triacetyl-beta-D-ribofuranosyl)-nicotinamide ("NR triacetate" or "NRTA"), 1-(2',3',5'-triacetyl-beta-D-ribofuranosyl)-1,4-dihydronicotinamide ("NRH triacetate" or "NRH-TA"), 1-(2',3',5'-triacetyl-beta-D-ribofuranosyl)-nicotinic acid ("NAR triacetate" or "NARTA"), or 1-(2',3',5'-triacetyl-beta-D-ribofuranosyl)-1,4-dihydronicotinic acid ("NARH triacetate" or "NARH-TA"), or a salt, prodrug, or solvate thereof, whereby skin cells are preserved viable.

BRIEF DESCRIPTIONS OF THE DRAWINGS

FIG. 1 depicts an oxidative damage protection assay of human epidermoid A431 cells in DMEM supplemented with fetal bovine serum ("FBS"), incubated with 1 mM $H_2O_2$; positive $H_2O_2$ control; +0.1 mM NRH triacetate ("NRH-TA," 2); +0.3 mM NRH triacetate (2); +1 mM NRH triacetate (2); +0.1 mM NARH triacetate ("NARH-TA," 4a); +0.3 mM NARH triacetate (4a); and +1 mM NARH triacetate (4a). Data is represented as percent cytoprotection in the presence of the test compound, calculated with respect to positive (1 mM $H_2O_2$) control.

Figure 4:
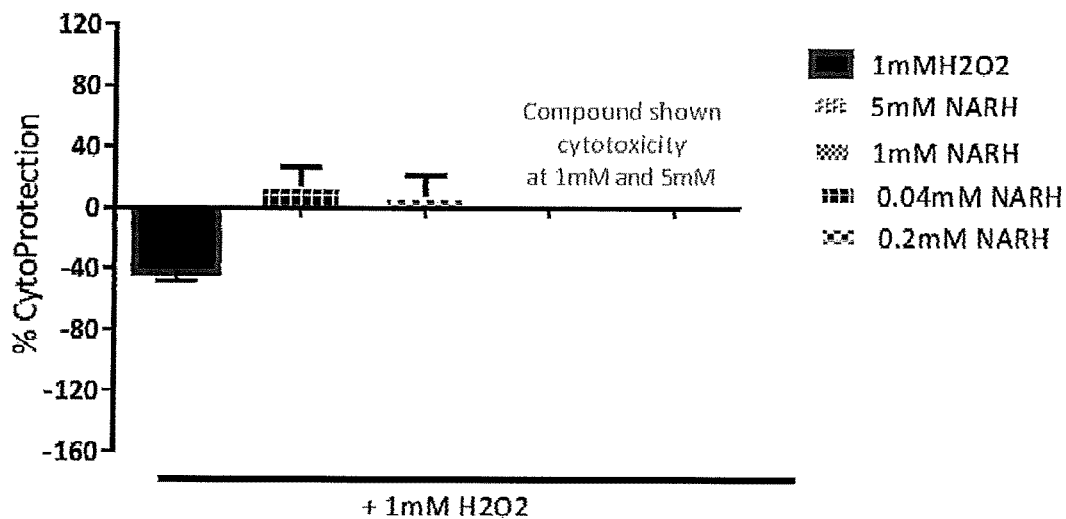

FIG. 4 depicts an oxidative damage protection assay of human epidermoid A431 cells in DMEM supplemented with FBS, incubated with 1 mM $H_2O_2$; positive $H_2O_2$ control; +5 mM reduced nicotinic acid riboside (NARH, II-H); +1 mM NARH (II-H); +0.04 mM NARH (II-H); and 0.2 mM NARH (II-H). Data is represented as percent cytoprotection in the presence of the test compound, calculated with respect to positive (1 mM $H_2O_2$) control.

Figure 5:
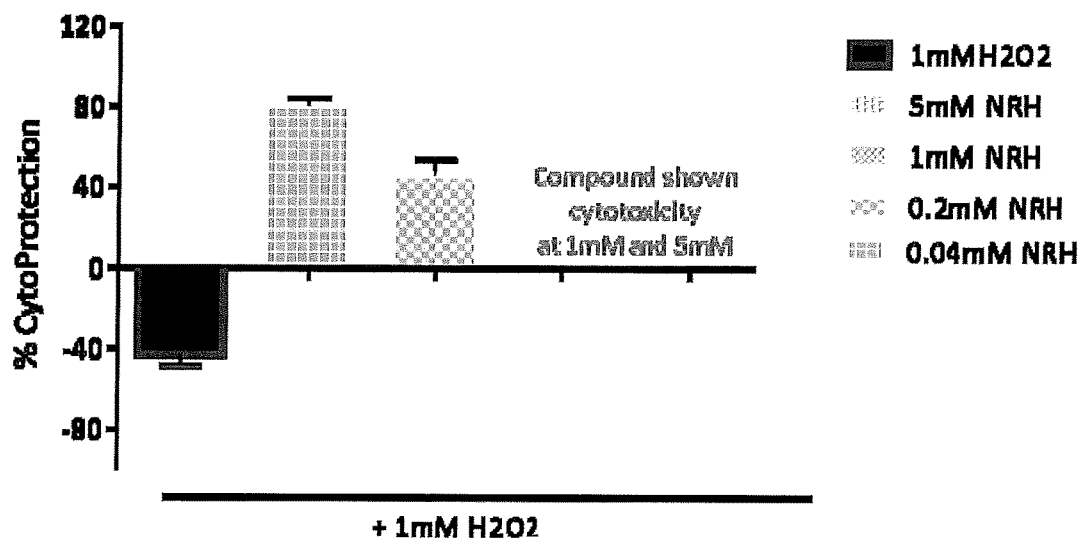

FIG. 5 depicts an oxidative damage protection assay of human epidermoid A431 cells in DMEM supplemented with FBS, incubated with 1 mM $H_2O_2$; positive $H_2O_2$ control; +5 mM reduced nicotinamide riboside (NRH, I-H); +1 mM NRH (I-H); +0.2 mM NRH (I-H); and +0.04 mM NRH (I-H). Data is represented as percent cytoprotection in the presence of the test compound, calculated with respect to positive (1 mM $H_2O_2$) control.

Figure 6:
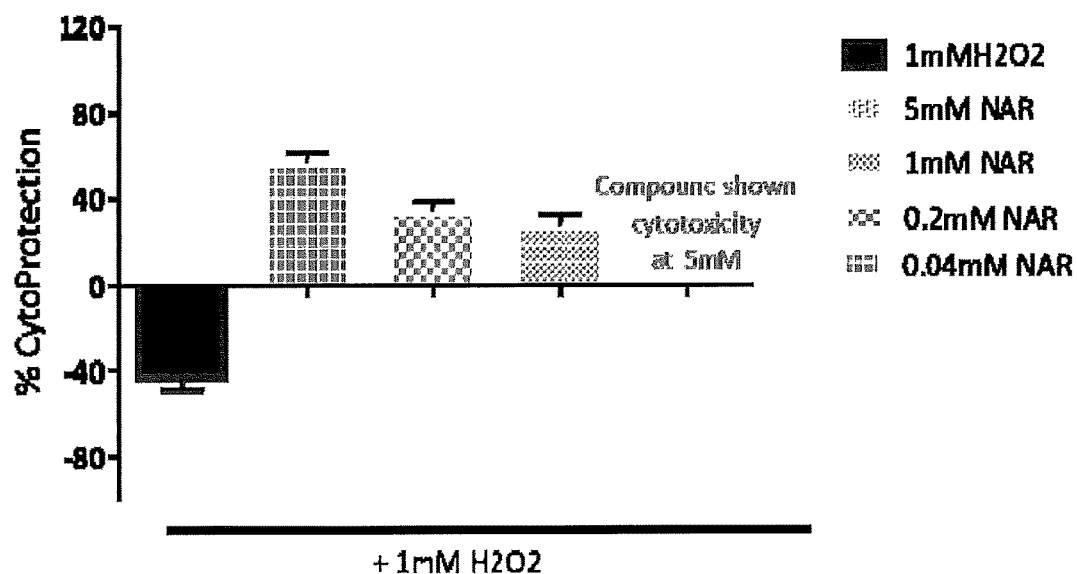

FIG. 6 depicts an oxidative damage protection assay of human epidermoid A431 cells in DMEM supplemented with FBS, incubated with 1 mM $H_2O_2$; positive $H_2O_2$ control; +5 mM nicotinic acid riboside (NAR, II); +1 mM NAR (II); +0.2 mM NAR (II); and +0.04 mM NAR (II). Data is represented as percent cytoprotection in the presence of the test compound, calculated with respect to positive (1 mM $H_2O_2$) control.

Figure 7:
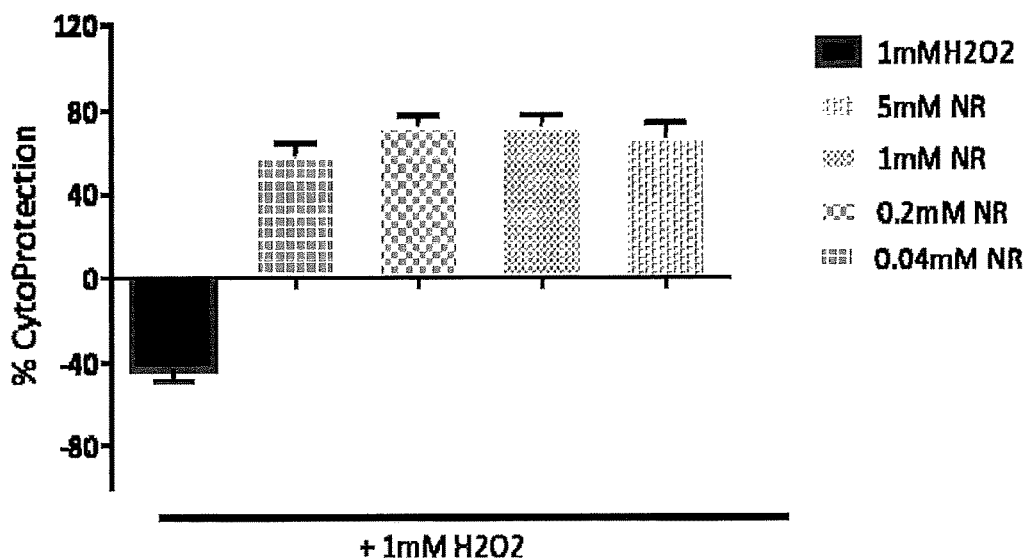

FIG. 7 depicts an oxidative damage protection assay of human epidermoid A431 cells in DMEM supplemented with FBS, incubated with 1 mM $H_2O_2$; positive $H_2O_2$ control; +5 mM nicotinamide riboside (NR, I); +1 mM NR (I); +0.2 mM NR (I); and +0.04 mM NR (I). Data is represented as percent cytoprotection in the presence of the test compound, calculated with respect to positive (1 mM $H_2O_2$) control.

Figure 8:
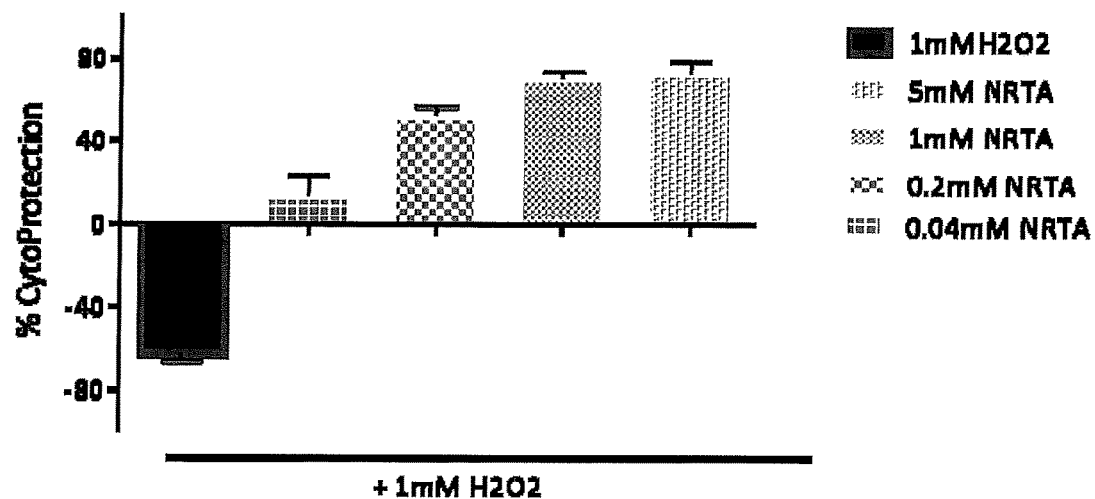

FIG. 8 depicts an oxidative damage protection assay of human epidermoid A431 cells in DMEM supplemented with FBS, incubated with 1 mM $H_2O_2$; positive $H_2O_2$ control; +5 mM nicotinamide riboside triacetate ("NR triacetate," alternatively "NRTA," 1); +1 mM NRTA (1); +0.2 mM NRTA (1); and +0.04 mM NRTA (1). Data is represented as percent cytoprotection in the presence of the test compound, calculated with respect to positive (1 mM $H_2O_2$) control.

Figure 9:
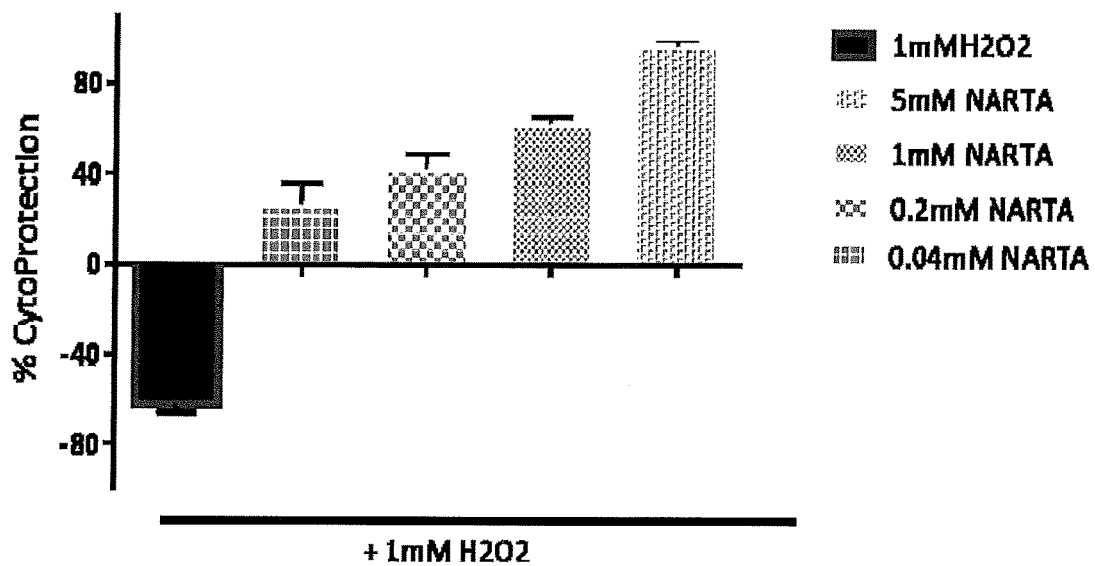

FIG. 9 depicts an oxidative damage protection assay of human epidermoid A431 cells in DMEM supplemented with FBS, incubated with 1 mM $H_2O_2$; positive $H_2O_2$ control; +5 mM nicotinic acid riboside triacetate ("NAR triacetate," alternatively "NARTA," 3); +1 mM NARTA (3); +0.2 mM NARTA (3); and +0.04 mM NARTA (3). Data is represented as percent cytoprotection in the presence of the test compound, calculated with respect to positive (1 mM $H_2O_2$) control.

DETAILED DESCRIPTION

NR, NAR, NRH, and NARH derivatives, prodrugs, solvates, or salts thereof were designed to facilitate delivery of NR or NAR (or their reduced forms NRH and NARH) into the skin (of a mammal, human, etc.). Specifically, these derivatives will have better efficacy in the skin due to their increased lipophilicity and the resulting more effective delivery. Increased skin permeation and the resulting more effective delivery of these NAD precursors will enhance their ability to be used in the care or treatment of skin and skin conditions. In some embodiments, the invention relates to NR, NAR, NRH, and NARH derivatives, prodrugs, solvates, or salts thereof. In further embodiments, the invention relates to pharmaceutical compositions and cosmetic compositions containing NR, NAR, NRH, and NARH derivatives, prodrugs, solvates, or salts thereof. In further embodiments, the invention relates to methods of using NR, NAR, NRH, and NARH derivatives, prodrugs, or salts thereof to promote the increase of intracellular levels of nicotinamide adenine dinucleotide (NAD+) in cells and tissues for improving cell and tissue survival and overall cell and tissue health. In further embodiments, the invention relates to derivatives of other established NAD+ precursor molecules (NMN, NaMN, and their reduced forms) that would facilitate enhanced delivery of these molecules to the skin.

In certain embodiments, nicotinamide riboside (NR) and 1,4-dihydronicotinamide riboside (NRH) derivatives, prodrugs, or salts thereof can increase NAD+ activity. In certain other embodiments, nicotinic acid riboside (NAR) and 1,4-dihydronicotinic acid riboside (NARH) derivatives, prodrugs, solvates, or salts thereof can increase NAD+ activity. It is also believed that increasing NAD+ activity can increase sirtuin activity because NAD+ can act as a substrate of SIRT1. Such agents can include NAD+ or NADH, a precursor of NAD+, an intermediate in the NAD+ salvage pathway, or a substance that generates NAD+, such as a nicotinamide mononucleotide adenylyltransferase ("NMNAT") or a nucleic acid encoding a nicotinamide mononucleotide adenylyltransferase. The nicotinamide mononucleotide adenylyltransferase can be an NMNAT1 protein. Other useful NAD+ precursors include nicotinamide and nicotinic acid. U.S. Pat. No. 7,776,326 to Milbrandt et al., incorporated by reference herein, discusses the NAD biosynthetic pathway.

In one embodiment, there is provided a method extending the lifespan of a cell, extending the proliferative capacity of a cell, slowing the aging of a cell, promoting the survival of a cell, delaying cellular senescence in a cell, mimicking the effects of calorie restriction on a cell, increasing the resistance of a cell to stress, or preventing apoptosis of a cell, by contacting the cells with nicotinamide riboside, derivatives, prodrugs, solvates, or salts thereof. In an exemplary embodiment, the methods comprise contacting skin cells with NR, NAR, NRH, or NARH derivatives, including derivatives, prodrugs, solvates, or salts thereof.

In another embodiment, cells that are intended to be preserved for long periods of time may be treated with NR, NAR, NRH, or NARH derivatives, including prodrugs, solvates, or salts thereof. The cells may be in suspension (e.g., blood cells, serum, biological growth media, etc.) or in tissues or organs. For example, blood collected from an individual for purposes of transfusion may be treated with NR, NAR, NRH, or NARH derivatives, including prodrugs or salts thereof, to preserve the blood cells for longer periods of time. Additionally, blood to be used for forensic purposes may also be preserved using NR, NRH, NAR, or NARH derivatives, including prodrugs, solvates, or salts thereof.

In some embodiments, the invention relates to the use of NR, NAR, NRH, or NARH derivatives, including prodrugs, solvates, or salts thereof, to prevent adverse effects and protect cells from toxicity, including use of NR, NAR, NRH, or NARH derivatives, including prodrugs, solvates, or salts thereof, to achieve a radioprotective effect. Toxicity may be an adverse effect of radiation, for example, as used in radiotherapy or laser surgery. Examples of toxins are radiation, such as UV or X-ray light. For example, radioprotection may be achieved by topical application of the compounds prior to radiotherapy or laser surgery. Radiative toxins have the potential to damage biological molecules such as DNA. This damage typically occurs by chemical reaction of the exogenous agent or its metabolites with biological molecules, or indirectly through stimulated production of reactive oxygen species (e.g., superoxide, peroxides, hydroxyl radicals). Repair systems in the cell excise and repair damage caused by toxins.

Particular cells that may be protected or treated to extend their lifespans or protect against apoptosis with NR, NAR, NRH, or NARH derivatives, including prodrugs, solvates, or salts thereof, include skin cells such as keratinocytes, melanocytes, dermal cells, epidermal cells, dendritic (Langerhans) cells, basal cells, squamous cells, stem cells, epidermal stem cells, hair follicles, and the like.

Other cells that may be treated to extend their lifespans or protect against apoptosis include cells for production, consumption, or food, e.g., cells from non-human mammals (such as meat) or plant cells (such as vegetables).

Nicotinamide riboside ("NR") is a pyridinium compound having the formula (I):

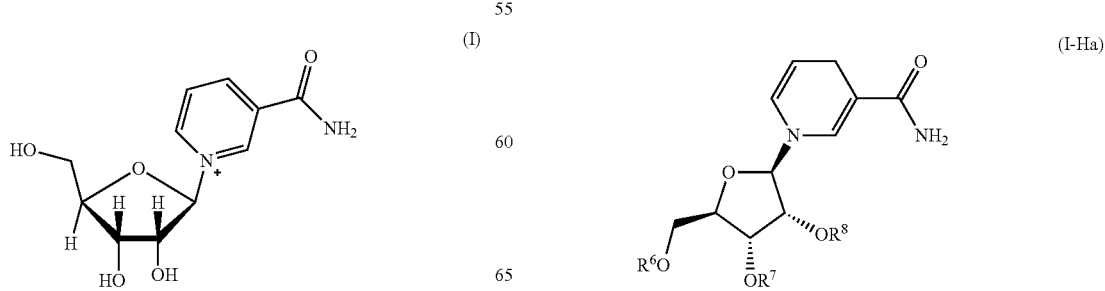

Nicotinamide riboside ("NR") is available in a reduced form ("NRH") as a 1,4-dihydropyridine compound having the formula (I-H):

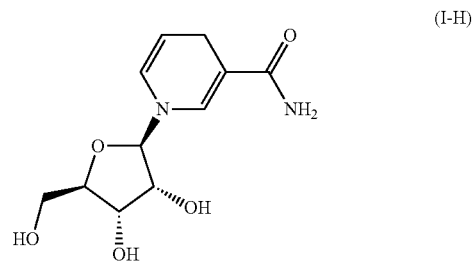 [SMILES: NC(=O)C1=CN([C@@H]2O[C@H](CO)[C@@H](O)[C@H]2O)C=CC1]

In a particular aspect, the compound (I) can be further derivatized to NR derivatives, prodrugs, or salts thereof, having the formula (Ia):

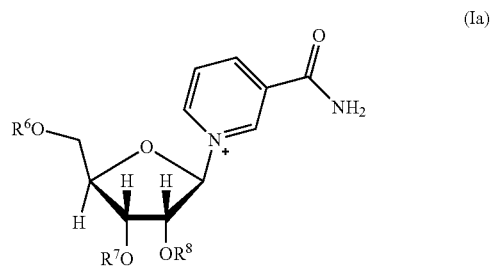

wherein $R^6$ is selected from the group consisting of hydrogen, —C(O)R', —C(O)OR', —C(O)NHR', substituted or unsubstituted $(C_1\text{-}C_8)$alkyl, substituted or unsubstituted $(C_3\text{-}C_8)$cycloalkyl, substituted or unsubstituted aryl, substituted or unsubstituted heteroaryl, and substituted or unsubstituted heterocycle;

R' is selected from the group consisting of hydrogen, —$(C_1\text{-}C_8)$alkyl, $(C_3\text{-}C_8)$cycloalkyl, aryl, heteroaryl, heterocycle, aryl$(C_1\text{-}C_4)$alkyl, and heterocycle$(C_1\text{-}C_4)$alkyl; and $R^7$ and $R^8$ are independently selected from the group consisting of hydrogen, —C(O)R', —C(O)OR', —C(O)NHR', substituted or unsubstituted $(C_1\text{-}C_8)$alkyl, substituted or unsubstituted $(C_3\text{-}C_8)$cycloalkyl, substituted or unsubstituted aryl, substituted or unsubstituted heteroaryl, substituted or unsubstituted heterocycle, substituted or unsubstituted aryl$(C_1\text{-}C_4)$alkyl, and substituted or unsubstituted heterocycle$(C_1\text{-}C_4)$alkyl.

In a particular aspect, the compound (I-H) can be further derivatized to NRH derivatives, prodrugs, or salts thereof having the formula (I-Ha):

wherein $R^6$, $R'$, $R^7$, and $R^8$ are as defined above for the compounds having the formulas (Ia).

In one preferred embodiment, the free hydrogens of hydroxyl groups on the ribose moiety can be substituted with acetyl groups ($CH_3$—$C(=O)$—) in a nicotinamide riboside compound having formula (I) to form compounds having formula (Ia), specifically 2',3',5'-triacetyl-nicotinamide riboside ("NR triacetate" or "NRTA"), having the formula (1). Alternative names include: 1-(2',3',5'-triacetyl-beta-D-ribofuranosyl)-nicotinamide, or 1-(3-carboxamido-pyridin-1-yl)-beta-D-riboside-2',3',5'-triacetate ("NR triacetate" or "NRTA," 1) all having the formula (1):

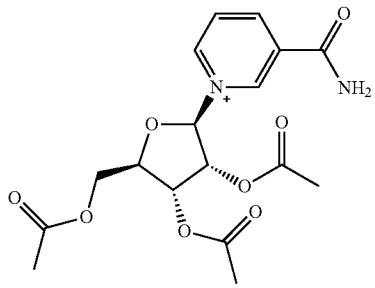

(1)

In another preferred embodiment, the free hydrogens of hydroxyl groups on the ribose moiety can be substituted with acetyl groups ($CH_3$—$C(=O)$—) in a 1,4-dihydronicotinamide compound having formula (I-H) to form compounds having formula (I-Ha), specifically 2',3',5'-triacetyl-1,4-dihydronicotinamide riboside ("NRH triacetate" or "NRH-TA"), having the formula (2). Alternative names include: 1-(2',3',5'-triacetyl-beta-D-ribofuranosyl)-1,4-dihydronicotinamide, or 1-(3-carboxamido-1,4-dihydropyridin-1-yl)-beta-D-riboside-2',3',5'-triacetate ("NRH triacetate" or "NRH-TA," 2) all having the formula (2):

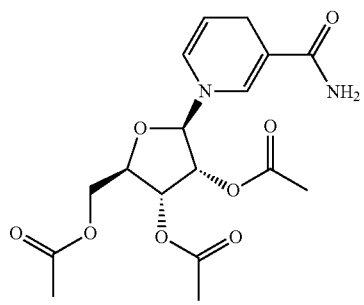

(2)

The compound of formula (2) was prepared in accordance with WO 2015/014722, which is hereby incorporated by reference herein.

Nicotinic acid riboside ("NaR," or "NAR") is a pyridinium compound having the formula (II):

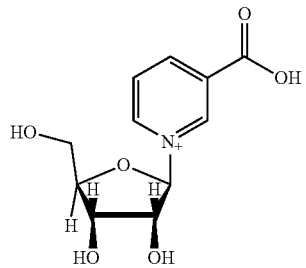

(II)

Nicotinic acid riboside ("NAR") is available in a reduced form ("NARH") as a 1,4-dihydropyridine compound having the formula (II-H):

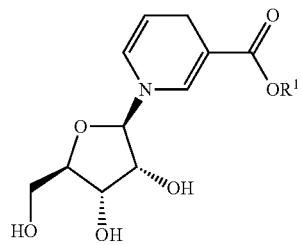

(II-H)

wherein $R^1$ is selected from hydrogen (II-Ha) and ($C_1$-$C_4$)alkyl (II-Hb), and prodrugs or salts thereof.

Compounds having the formula (II-H) may be prepared in accordance with WO 2015/014722, which is incorporated by reference. Depending on the selection of $R^1$, compounds having the formula (II-H): include alkyl 1-(beta-D-ribofuranosyl)-1,4-dihydronicotinates or alternatively alkyl 1,4-dihydronicotinate riboside ("alkyl NARH") where $R^1$ is selected from ($C_1$-$C_4$)alkyl (II-Hb); and include 1-(beta-D-ribofuranosyl)-1,4-dihydronicotinic acid where $R^1$ is selected from hydrogen (II-Ha).

In a particular aspect, a compound having the formula (II) can be further derivatized to NAR derivatives, prodrugs, solvates, or salts thereof having the formula (IIa):

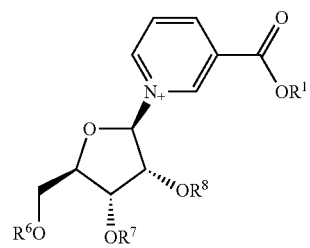

(IIa)

wherein $R^1$, $R^6$, $R'$, $R^7$, and $R^8$ are as defined above for compounds having the formulas (Ia), (I-Ha), and (II-H).

In a preferred embodiment, the free hydrogens of hydroxyl groups on the ribose moiety of a compound having formula (II) can be substituted with acetyl groups ($CH_3$—$C(=O)$—) in a nicotinic acid riboside compound to form an NAR derivative, prodrug, or salt thereof, having the formula (IIa), specifically 1-(2',3',5'-triacetyl-beta-D-ribofuranosyl)-nicotinic acid ("NAR triacetate" or "NARTA") where $R^1$ is hydrogen, having the formula (3). Alternative names include: 1-(2',3',5')-triacetyl-beta-D-ribofuranosyl)-nicotinic acid, or 1-(3-carboxyl-pyridin-1-yl)-beta-D-riboside-2',3',5'-triacetate ("NAR triacetate" or "NARTA," 3) all having the formula (3):

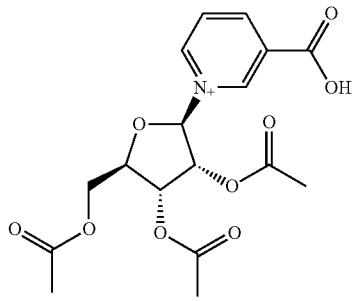

(3)

In a particular aspect, a compound having the formula (II-H) can be further derivatized to NARH derivatives, prodrugs, solvates, or salts thereof having the formula (II-Hc):

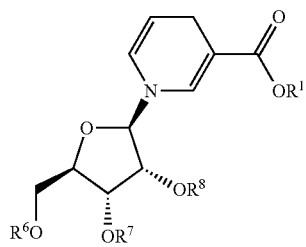

(II-Hc)

wherein $R^1$, $R^6$, $R'$, $R^7$, and $R^8$ are as defined above for the compounds having the formulas (Ia), (I-Ha), (II-H), and/or (IIa).

In one preferred embodiment, the free hydrogens of hydroxyl groups on the ribose moiety of a compound having formula (II-H) can be substituted with acetyl groups ($CH_3$—C(=O)—) in a 1,4-dihydropyridine compound to form an NARH derivative, prodrug, solvate, or salt thereof, having the formula (II-Hc), specifically a compound having formula (4), which, depending on the selection of $R^1$: include alkyl 2',3',5'-triacetyl-1,4-dihydronicotinate riboside ("alkyl NARH triacetate"), alternatively called alkyl 1-(2',3',5'-triacetyl-beta-D-ribofuranosyl)-1,4-dihydronicotinate ("alkyl NARH triacetate"), where $R^1$ is selected from ($C_1$-$C_4$)alkyl; and include 2',3',5'-triacetyl-1,4-dihydronicotinic acid riboside ("NARH triacetate" "NARH-TA"), alternatively called 1-(2',3',5'-triacetyl-beta-D-ribofuranosyl)-1,4-dihydronicotinic acid ("NARH triacetate" or "NARH-TA"), where $R^1$ is selected from hydrogen

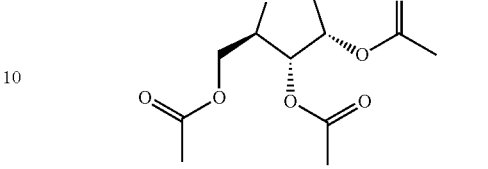

(4)

wherein $R^1$ is selected from hydrogen and ($C_1$-$C_4$)alkyl, and salts, solvates, or prodrugs thereof.

In a particularly preferred embodiment, $R^1$ is hydrogen (compound 4a), also known as 2',3',5'-triacetyl-1,4-dihydronicotinic acid riboside ("NARH triacetate" or "NARH-TA," 4a), or 1-(2',3',5'-triacetyl-beta-D-ribofuranosyl)-1,4-dihydronicotinic acid, or alternatively 1-(3-carboxy-1,4-dihydropyridin-1-yl)-beta-D-riboside-2',3',5'-triacetate ("NARH triacetate" or "NARH-TA," 4a). The compound of formula (4a) was prepared in accordance with WO 2015/014722, which is hereby incorporated by reference herein.

The compounds having formula (4) where $R^1$ is hydrogen ("NARH triacetate," "NARH-TA," 4a) may also exist as a conjugate base salt wherein hydrogen is replaced with a salt counterion such as, but not limited to, sodium, potassium, lithium, magnesium, and the like. Reference is made to: the latest edition of REMINGTON'S PHARMACEUTICAL SCIENCES (Mack Publishing Co., Easton, Pa.); S. Berge et al., *Pharmaceutical Salts*, 66 J. PHARM. SCI. 1 (1977) (and references cited therein); and L. D. Bighley, et al., *Salt Forms of Drugs and Absorption*, in ENCYCLOPEDIA PHARM. TECH. VOL. 13 453 (J. Swarbrick ed., Marcel Dekker, Inc. 1996) (and references cited therein); all incorporated by reference herein.

In an embodiment, compounds having formulas selected from (Ia), (I-Ha), (IIa), (II-H), (II-Ha), (II-Hb), and (II-Hc) possess certain properties believed to enhance use as a topical skin agent or use in topical skin formulations. For example, these compounds have increased lipophilicity in their reduced forms.

Forms of NR, NAR, NMN, NAMN, NRH, NARH are disclosed herein that enhance the permeation characteristics of these molecules for more effective topical delivery to skin. Chemical permeation enhancers facilitate drug permeation across the skin by increasing drug partitioning into the barrier domain of the stratum corneum, increasing drug diffusivity in the barrier domain of the stratum corneum or the combination of both (Thong et al., *Percutaneous penetration enhancers: an overview*, 20 SKIN PHARMACOL. PHYSIOL. 272 (2007)). Many substances have been shown to have skin permeabilization potential. Useful permeation enhancers include, but are not limited to, the following categories: alcohols (ethanol, pentanol, benzyl alcohol, lauryl alcohol, propylene glycols, and glycerol), fatty acids (linoleic acid, oleic acid, and lauric acid), amines, esters (ethyl acetate), amides, hydrocarbons, surfactants, terpenes, sulfoxides (dimethyl sulfoxide, i.e., DMSO), and phospholipids (lecithin). See K. S. Paudel et al., *Challenges and opportunities in dermal/transdermal delivery*, 1 THER. DELIV. 109 (2010) (and references cited therein), incorporated by reference herein.

NR, NAR, NRH, or NARH derivatives, including prodrugs, solvates, or salts thereof, may also be applied during developmental and growth phases in mammals, plants, insects, or microorganisms, in order to, e.g., alter, retard, or accelerate the developmental and/or growth process.

In another embodiment, the NRH or NARH derivatives, including prodrugs, solvates, or salts thereof, disclosed herein will be more effective at penetrating the skin where they can exert their beneficial effects. The same is true for the NR, NAR, NMN, or NAMN derivatives described herein. All of these derivatives are predicted to increase intracellular levels of nicotinamide adenine nucleotide (NAD+) in cells and tissues for improving cell and tissue survival and overall cell and tissue health.

In another embodiment, NR, NAR, NRH, or NARH derivatives, including prodrugs, solvates, or salts thereof, may be used to treat cells useful for transplantation or cell therapy, including, for example, solid tissue grafts, organ transplants, cell suspensions, stem cells, bone marrow cells, etc. The cells or tissue may be an autograft, an allograft, a syngraft, or a xenograft. The cells or tissue may be treated with the NR, NAR, NRH, or NARH derivatives, including prodrugs, solvates, or salts thereof, prior to administration/implantation, currently with administration/implantation, and/or post administration/implantation into a subject. The cells or tissue may be treated prior to removal of the cells from the donor individual, ex vivo after removal of the cells or tissue from the donor individual, or post-implantation into the recipient. For example, the donor or recipient individual may be treated systematically with NR, NAR, NRH, or NARH derivatives, including prodrugs, solvates, or salts thereof, or may have a subset of cells/tissue treated locally with nicotinamide riboside, prodrugs, solvates, or salts thereof. In certain embodiments, the cells or tissue (or donor/recipient individuals) may be treated with one or more additional therapeutic agents useful for prolonging graft survival, such as, for example, an immunosuppressant agent, a cytokine, an angiogenic factor, etc.

In yet other embodiments, cells may be treated with NR, NAR, NRH, or NARH derivatives, including prodrugs, solvates, or salts thereof, which increase the level of NAD+ in vivo, e.g., to increase their lifespan or prevent apoptosis. For example, in a principal embodiment, skin can be protected from aging (e.g., developing wrinkles, loss of elasticity, etc.) by treating skin or epithelial cells with NR, NAR, NRH, or NARH derivatives, including prodrugs or salts thereof, which increases the level of intracellular NAD+. Exemplary skin afflictions or skin conditions that may be treated in accordance with the methods described herein include disorders or diseases associated with or caused by inflammation, sun damage, or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer, and the effects of natural aging. In another embodiment, NR, NAR, NRH, or NARH derivatives, including prodrugs or salts thereof, which increase the level of intracellular NAD+, may be used for the treatment of wounds and/or burns to promote healing, including, for example, first-, second-, or third-degree burns and/or thermal, chemical, or electrical burns. The formulations may be administered topically, to the skin or mucosal tissue, as an ointment, lotion, cream, microemulsion, gel, solution, or the like, as further described herein, within the context of a dosing regimen effective to bring about the desired result.

Topical formulations comprising one or more of NR, NAR, NRH, or NARH derivatives, including prodrugs or salts thereof, that increases the level of intracellular NAD+ may also be used as preventive, e.g., chemopreventive, compositions. When used in a chemopreventive method, susceptible skin is treated prior to any visible condition in a particular individual.

In all of the above hypotheses, compounds having formulas (Ia), (I-Ha), (IIa), (II-H), (II-Ha), (II-Hb), and (II-Hc) may be used in the care or treatment of skin and skin conditions. The overall effects and advantages shown by compounds having formulas (Ia), (I-Ha), (IIa), (II-H), (II-Ha), (II-Hb), and (II-Hc) as described herein may be enhanced due to better delivery to the skin. In an example, the overall effects and advantages shown by compounds having formulas (Ia), (I-Ha), (IIa), (II-H), (II-Ha), (II-Hb), and (II-Hc) as described herein may be enhanced due to better transdermal delivery and bioavailability.

Topical formulations may include other NAD+ precursors, or compounds capable of increasing NAD+ in vivo, such as, but not limited to, NR, NAR, NRH, or NARH derivatives, including prodrugs or salts thereof. In a preferred embodiment, the topical formulations can include NR triacetate (1) (or "NRTA"), NRH triacetate (2) (or "NRH-TA"), NAR triacetate (3) (or "NARTA"), and NARH triacetate (4a) (or "NARH-TA") as described.

Useful ranges of NR, NAR, NRH, or NARH derivatives, including prodrugs, solvates, or salts thereof, in the topical compositions include from about 0.001% to about 50% by weight, based on the total weight of the composition. Another suitable range for NR, NAR, NRH, or NARH derivatives, including prodrugs, solvates, or salts thereof, is from about 0.1% to about 10% by weight, based on the total weight of the composition. Another suitable range for NR, NAR, NRH, or NARH derivatives, including prodrugs, solvates, or salts thereof, is from about 0.5% to about 5% by weight, based on the total weight of the composition. Another suitable range for NR, NAR, NRH, or NARH derivatives, including prodrugs, solvates, or salts thereof, is from about 1% to about 2% by weight, based on the total weight of the composition.

Oral formulations of one or more NR, NAR, NRH, or NARH derivatives, including prodrugs, solvates, or salts thereof, are contemplated. Useful therapeutic dosages of one or more NR, NAR, NRH, or NARH derivatives, including prodrugs, solvates, or salts thereof, can range, but are not limited to, from about 1 mg to about 5000 mg in a human individual. Another suitable dose range is from about 5 mg to about 500 mg. Another suitable dose range is from about 50 mg to about 500 mg. NR, NAR, NRH, or NARH derivatives, including prodrugs, solvates, or salts thereof, may be formulated orally or topically as a pharmaceutical or nutraceutical composition, including a pharmaceutically or nutraceutically acceptable carrier, respectively. In one embodiment of a pharmaceutical composition containing NR, NAR, NRH, or NARH derivatives, including prodrugs, solvates, or salts thereof, a suitable level of one or more of NR, NAR, NRH, or NARH derivatives may range from about 0.01% by weight to about 50% by weight, based on the total weight of the composition. In another embodiment of a pharmaceutical composition containing NR, NAR, NRH, or NARH derivatives, including prodrugs, solvates, or salts thereof, a suitable level of one or more of NR, NAR, NRH, or NARH derivatives may range from about 0.1% by weight to about 10% by weight, based on the total weight of the composition.

Human skin comprises a top epidermal layer (epidermis), which rests on a lower dermal layer (dermis). The epidermis is made up primarily of keratinocytes, which develop at the bottom, move toward the top, and are constantly replaced. As old dead cells are shed, they are replaced, so this layer is constantly renewing itself. The epidermis also contains melanocytes, located generally near the bottom of the layer and which produce the pigment melanin, which contributes to skin color and provides UV-protection. The epidermis also contains dendritic (Langerhans) cells, which are involved in the immune system, and basal cells found at the bottom of the layer. The epidermis also includes squamous cells. The epidermal and dermal layers also contain stem cells and hair follicles. In mammals, melanocytes are also distributed in the brain, eye, ear, and heart, among other tissues.

The skin cells, as described, are susceptible to UV-light-induced damage, DNA damage, and carcinogenesis. Additionally, normal aging contributes to formation of wrinkles, age spots, loss of skin elasticity, and other signs of aging, including superficial wrinkles, a coarse deep wrinkle, enlarged pores, photodamage, scaliness, flakiness, dryness, sagging in skin, puffiness in skin around eye, puffiness in skin around jowl, loss of skin firmness, loss of skin tightness, loss of barrier function, loss of skin recoil from deformation, discoloration, blotching, sallowness, hyperpigmentation, keratosis, hyperkeratinization, elastosis or collagen breakdown, and cellulite, or combinations thereof.

Therefore, in an embodiment, one or more NR, NAR, NRH, or NARH derivatives, including prodrugs or salts thereof, may be used as follows: to improve the signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of barrier function, loss of skin recoil from deformation, discoloration, blotching, sallowness, hyperpigmentation, keratosis, hyperkeratinization, elastosis or collagen breakdown, and cellulite, or combinations thereof.

The cosmetic or cosmeceutical compositions of the present invention containing one or more NR, NAR, NRH, or NARH derivatives, including prodrugs, solvates, or salts thereof, may be administered in combination with a nutraceutically acceptable carrier. The active ingredients in such formulations may comprise from 1% by weight to 99% by weight, or alternatively, 0.1% by weight to 99.9% by weight.

The topical pharmaceutical compositions of the present invention containing one or more NR, NAR, NRH, or NARH derivatives, including prodrugs, solvates, or salts thereof, may be administered in combination with a pharmaceutically acceptable carrier. The active ingredients in such formulations may comprise from 1% by weight to 99% by weight, or alternatively, 0.1% by weight to 99.9% by weight.

In accordance with certain embodiments, the cosmetic and/or topical pharmaceutical compositions disclosed herein can be provided in the form of an ointment, cream, lotion, gel, or other transdermal delivery systems as described in L V. ALLEN, JR. ET AL., ANSEL'S PHARMACEUTICAL DOSAGE FORMS AND DRUG DELIVERY SYSTEMS 272 (9th ed., Lippincott Williams & Wilkins 2011), which is incorporated by reference herein.

Transdermal preparations may be formed from an ointment, cream, or gel that has been combined with a penetration enhancer and are designed to deliver an active or medicinal ingredient systematically.

Other suitable semi-solid forms for use as cosmetic and/or topical pharmaceutical compositions include pastes and glycerogelatins.

In other embodiments the topical and/or cosmetic compositions can be prepared in accordance with dosage forms as described in SAMPLE PREPARATION OF PHARMACEUTICAL DOSAGE FORMS (B. Nickerson ed., Springer 2011), incorporated by reference herein.

Topical formulations comprising pterostilbene may also be used in preventive, e.g., chemopreventive, or protective, e.g., cytoprotective, compositions. When used in a chemopreventive or cytoprotective method, susceptible skin is treated prior to any visible condition in a particular individual.

One useful dosage range for topical pterostilbene is from about 0.1% by weight to about 10% by weight, based on the total weight of the composition. Another suitable dosage range for topical pterostilbene is from about 1-2% by weight, based on the total weight of the composition.

Useful oral therapeutic dosages of pterostilbene can range, but are not limited to, from about 1 mg to about 1000 mg in a human individual. Another suitable dose range is from about 5 mg to about 500 mg. Another suitable dose range is from about 20 mg to about 250 mg. Pterostilbene may be formulated as a pharmaceutical or nutraceutical composition, including a pharmaceutically or nutraceutically acceptable carrier, respectively. In one embodiment of a pharmaceutical composition containing pterostilbene, a suitable level of pterostilbene may range from about 0.1% by weight to about 10% by weight, based on the total weight of the composition.

Definitions

As used in the specification and the appended claims, the singular forms of "a," "an," and "the" include plural referents unless the context clearly dictates otherwise.

As used herein, the terms "nutraceutically acceptable carrier" and "pharmaceutically acceptable carrier" mean any carrier, diluent, or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use, an oil-base is preferred.

As used herein, the term "penetration enhancer" means or includes, for example, dimethyl sulfoxide, ethanol, propylene glycol, glycerin, PEG, urea, dimethyl sulfoxide, ethanol, propylene glycol, glycerin, PEG, urea, dimethyl acetamide, sodium lauryl sulfate, poloxamers, Spans, Tweens, lecithin, and/or terpenes amongst others.

As used herein, the term "paste" means a preparation containing a larger proportion of solid material rendering them stiffer than ointments.

As used herein, the term "glycerogelatin" means a plastic mass containing gelatin, glycerin, water, and an active or medicinal ingredient.

As used herein, the term "ointment" means a semi-solid preparation including an ointment base having one or more active ingredients incorporated or fused (i.e., melted together with other components of the formulation and cooled with constant stirring to form a congealed preparation) therein. The ointment base may be in the form of: an oleaginous or hydrocarbon base (e.g., petrolatum or a petrolatum/wax combination); an absorption base that permits the incorporation of aqueous solution resulting in the formation of a water-in-oil emulsion (e.g., hydrophilic petrolatum) or that is a water-in-oil that permits the incorporation of additional quantities of aqueous solutions (e.g., lanolin); a water-removable base that is an oil-in-water emulsion that may be diluted with water or aqueous solutions (e.g., hydrophilic ointment, USP); or a water-soluble base that do not contain oleaginous components (e.g., polyethylene glycol ("PEG") formulations that combine PEGs having an average molecular weight below 600 with a PEG having an average molecular weight above 1,000); and the like.

As used herein, the term "cream" means a semi-solid preparation containing one or more active or medicinal agent dissolved or dispersed in either a water-in-oil emulsion or an oil-in-water emulsion or in another type of water-washable base. Generally, creams are differentiated from ointments by the ease with which they are applied/spread onto a surface such as the skin and the ease with which they are removed from a treated surface.

As used herein, the term "lotion" means a suspension of solid materials in an aqueous vehicle. Generally, lotions have a less greasy character and increased spreadability over large areas of the skin than do ointments, creams, and gels.

As used herein, the term "gel" means a semisolid system including a dispersion of small and/or large molecules in an aqueous liquid vehicle that is rendered jellylike by the addition of a gelling agent. Suitable gelling agents include, but are not limited to, synthetic macromolecules (e.g., carbomer polymers), cellulose derivatives (e.g., carboxymethylcellulose and/or hydroxypropyl methylcellulose), and natural gums (e.g., tragacanth gum, carrageenan, and the like). Gel preparations may be in the form of a single-phase gel in which the active or medicinal ingredients are uniformly dispersed throughout the liquid vehicle without visible boundaries or a two-phase gel, wherein flocculants or small distinct particles of the active or medicinal ingredient are dispersed within the liquid vehicle.

As used herein, the term "alkyl," by itself or as part of another substituent, means, unless otherwise stated, a straight, branched, or cyclic chain hydrocarbon (cycloalkyl) having the number of carbon atoms designated (i.e., $C_1$-$C_6$ means one to six carbons). Examples include methyl, ethyl, propyl, isopropyl, butyl, isobutyl, tert-butyl, pentyl, neopentyl, hexyl, cyclohexyl, and cyclopropyl. Most preferred are ($C_1$-$C_3$)alkyl, particularly ethyl, ethyl, and isopropyl.

As used herein, the term "alkenyl," by itself or as part of another substituent, means, unless otherwise stated, a stable mono-unsaturated or di-unsaturated straight chain, the unsaturation meaning a carbon-carbon double bond (—CH═CH—), branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl, and the higher homologs and isomers. Functional groups representing an alkene are exemplified by —CH═CH—CH$_2$— and CH$_2$═CH—CH$_2$—.

As used herein, the terms "substituted alkyl" or "substituted alkenyl" mean "alkyl" or "alkenyl," respectively, as defined above, substituted by one, two, or three substituents. The substituents may, for example, be selected from the group consisting of halogen, —OH, —NH$_2$, —N(CH$_3$)$_2$, —CO$_2$H, —CO$_2$(C$_1$-C$_4$)alkyl, methoxy, ethoxy, trifluoromethyl, —C(═O)NH$_2$, —SO$_2$NH$_2$, —C(═NH)NH$_2$, —C≡N, and —NO$_2$, preferably selected from halogen and —OH. Examples of substituted alkyls include, but are not limited to, 2,2-difluoromethyl, 2-carboxycyclopentyl, and 3-chloropropyl.

As used herein, the term "alkynyl," by itself or as part of another substituent, means, unless otherwise stated, a stable carbon-carbon triple bond-containing radical (—C≡C—), branched chain or cyclic hydrocarbon group having the stated number of carbon atoms. Examples include ethynyl and propargyl.

As used herein, the term "alkoxy," by itself or as part of another substituent, means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

As used herein, the terms "carbamyl" or "carbamoyl" means the group —C(═O)NRR', wherein R and R' are independently selected from hydrogen or a hydrocarbyl functional group, or wherein R and R' combined form a heterocycle. Examples of carbamyl groups include: —C(═O)NH$_2$ and —C(═O)N(CH$_3$)$_2$.

As used herein, the term "cyano," by itself or as part of another substituent, means, unless otherwise stated, a —C≡N group.

As used herein, the term "heteroaryl," by itself or as part of another substituent, means, unless otherwise stated, a stable straight or branched chain alkyl group consisting of the stated number of carbon atoms and one or two heteroatoms selected from the group consisting of oxygen, nitrogen, and sulfur, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, CH$_2$—CH$_2$—NH—CH$_3$, —CH$_2$—S—CH$_2$—CH$_3$, and —CH$_2$—CH$_2$—S(═O)—CH$_3$. Up to two heteroatoms may be consecutive, such as, for example, —CH$_2$—NH—OCH$_3$, or —CH$_2$—CH$_2$—S—S—CH$_3$.

As used herein, the terms "halo" or "halogen," by themselves or as part of another substituent, mean, unless otherwise stated, a monovalent fluorine, chlorine, bromine, or iodine atom.

As used herein, the term "nitro," by itself or as part of another substituent, means, unless otherwise stated, a —NO$_2$ group.

As used herein, the term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —CF$_3$.

As used herein, the term "aromatic" generally refers to a carbocycle or heterocycle having one or more polyunsaturated rings having aromatic character (i.e. having (4n+2) delocalized π (pi) electrons where n is an integer).

As used herein, the term "aryl," by itself or as part of another substituent, means, unless otherwise stated, a carbocyclic aromatic system containing one or more rings (typically one, two, or three rings) wherein such rings may be attached together in a pendant manner, such as a biphenyl, or may be fused, such as naphthalene. Examples include phenyl; anthracyl; and naphthyl. Preferred are phenyl and naphthyl, most preferred is phenyl.

As used herein, the terms "heterocycle," "heterocyclyl," or "heterocyclic," by itself or as a part of another substituent, means, unless otherwise stated, an unsubstituted or substituted, stable, mono- or multi-cyclic heterocyclic ring system that consists of carbon atoms and at least one heteroatom independently selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

As used herein, the terms "heteroaryl" or "heteroaromatic," by itself or as a part of another substituent, means, unless otherwise stated, a heterocycle having aromatic character. Similarly, the term "heteroaryl($C_1$-$C_3$)alkyl" means a functional group wherein a one to three carbon alkylene chain is attached to a heteroaryl group, e.g., —$CH_2$—$CH_2$-pyridyl. The term "substituted heteroaryl($C_1$-$C_3$)alkyl" means a heteroaryl($C_1$-$C_3$)alkyl functional group in which the heteroaryl group is substituted. A polycyclic heteroaryl may include fused rings. Examples include indole, 1H-indazole, 1H-pyrrolo[2,3-b]pyridine, and the like. A polycyclic heteroaryl may include one or more rings that are partially saturated. Examples include indoline, tetrahydroquinoline, and 2,3-dihydrobenzofuryl.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophene, piperidine, 1,2,3,6-tetrahydropyridine, piperazine, N-methylpiperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl, and 1,3,4-oxadiazolyl.

Polycyclic heterocycles include both aromatic and non-aromatic polycyclic heterocycles. Examples of polycyclic heterocycles include: indolyl, particularly 3-, 4-, 5-, 6-, and 7-indolyl; indolinyl; indazolyl, particularly 1H-indazol-5-yl; quinolyl; tetrahydroquinolyl; isoquinolyl, particularly 1- and 5-isoquinolyl; 1,2,3,4-tetrahydroisoquinolyl; cinnolyl; quinoxalinyl, particularly 2- and 5-quinoxalinyl; quinazolinyl; phthalazinyl; 1,8-naphthyridinyl; 1,4-benzodioxanyl; coumaryl; dihydrocoumaryl; naphthyridinyl, particularly 3,4- and 1,5-naphthyridinyl; benzofuryl, particularly 5-, 6-, and 7-benzofuryl; 2,3-dihydrobenzofuryl; 1,2-benzisoxazolyl; benzothienyl, particularly 3-, 4-, 5-, 6-, and 7-benzothienyl; benzoxazolyl; benzothiazolyl, particularly 2-benzothiazolyl and 5-benzothiazolyl; purinyl; benzimidazolyl, particularly 2-benzimidazolyl; benzotriazolyl; thioxanthinyl; carbazolyl; carbolinyl; acridinyl; pyrrolizidinyl; pyrrolo[2,3-b]pyridinyl, particularly 1H-pyrrolo[2,3-b]pyridine-5-yl; and quinolizidinyl. Particularly preferred are 4-indolyl, 5-indolyl, 6-indolyl, 1H-indazol-5-yl, and 1H-pyrrolo[2,3-b]pyridine-5-yl.

The aforementioned listing of heterocyclyl and heteroaryl moieties is intended to be representative and not limiting.

As used herein, the term "substituted" means, unless otherwise stated, that an atom or group of atoms has replaced hydrogen as the substituent attached to another group. For aryl and heteroaryl groups, the term "substituted" refers, unless otherwise stated, to any level of substitution, namely mono-, di-, tri-, tetra-, or penta-substitution, where such substitution is permitted. The substituents are independently selected, and substitution may be at any chemically accessible position.

As used herein, the term "aryl($C_1$-$C_3$)alkyl," by itself or as part of another substituent, means, unless otherwise stated, a functional group wherein a ($C_1$-$C_3$)alkylene chain is attached to an aryl group, e.g., —$CH_2$—$CH_2$-phenyl. Examples include aryl($CH_2$)— and aryl($CH(CH_3)$)—. As used herein, the term "substituted aryl($C_1$-$C_3$)alkyl," by itself or as part of another substituent, means, unless otherwise stated, means an aryl($C_1$-$C_3$)alkyl functional group in which the aryl group is substituted. Preferred is substituted aryl($CH_2$)—. Similarly, as used herein, the term "heterocycle($C_1$-$C_3$)alkyl," by itself or as part of another substituent, means, unless otherwise stated, a functional group wherein a ($C_1$-$C_3$)alkylene chain is attached to a heterocyclic group, e.g., morpholino-$CH_2$—$CH_2$—. As used herein, the term "substituted heteroaryl($C_1$-$C_3$)alkyl" means a heteroaryl($C_1$-$C_3$)alkyl functional group in which the heteroaryl group is substituted.

Synthetic Preparations of Compounds Having Formulas (Ia), (I-Ha), (IIa), (II-H), (II-Ha), (II-Hb), and (II-Hc)

The present invention further embraces isolated compounds having formulas (Ia), (I-Ha), (IIa), (II-H), (II-Ha), (II-Hb), and (II-Hc). The expression "isolated compound" refers to a preparation of a compound having a formula selected from (Ia), (I-Ha), (IIa), (II-H), (II-Ha), (II-Hb), and (II-Hc), or a mixture of compounds having formulas selected from (Ia), (I-Ha), (IIa), (II-H), (II-Ha), (II-Hb), and (II-Hc), wherein the isolated compound or compounds has been separated from the reagents used, and/or byproducts formed, in the synthesis of the compound or compounds. "Isolated" does not mean that the preparation is technically pure (homogeneous), but that the preparation is sufficiently pure to compound in a form in which the preparation can be used therapeutically. Preferably an "isolated compound" refers to a preparation of a compound having a formula selected from (Ia), (I-Ha), (IIa), (II-H), (II-Ha), (II-Hb), and (II-Hc), or a mixture of compounds having formulas selected from (Ia), (I-Ha), (IIa), (II-H), (II-Ha), (II-Hb), and (II-Hc), which contains the named compound or mixture of compounds having formulas selected from (Ia), (I-Ha), (IIa), (II-H), (II-Ha), (II-Hb), and (II-Hc) in an amount of at least 10 percent by weight of the total weight. Preferably, the preparation contains the named compound or mixture of compounds in an amount of at least 50 percent by weight of the total weight; more preferably, at least 80 percent by weight of the total weight; and most preferably, at least 90 percent, at least 95 percent, or at least 98 percent by weight of the total weight of the preparation.

The compounds of the invention, and intermediates, may be isolated from their reaction mixtures and purified by standard techniques such as: filtration; liquid-liquid extraction; solid phase extraction; distillation; recrystallization; or chromatography, including flash column chromatography, preparative TLC, HPTLC, or HPLC. The preferred method for purification of the compounds having formulas selected from (Ia), (I-Ha), (IIa), (II-H), (II-Ha), (II-Hb), and (II-Hc) or salts thereof comprises crystallizing the compound or salt from a solvent to form, preferably, a crystalline form of the compounds or salts thereof. Following crystallization, the crystallization solvent is removed by a process other than evaporation, for example filtration or decanting, and the crystals are then preferably washed using pure solvent (or a mixture of pure solvents). Preferred solvents for crystallization include: water; alcohols, particularly alcohols containing up to four carbon atoms such as methanol, ethanol, isopropanol, and butan-1-ol, butan-2-ol, and 2-methyl-2-propanol; ethers, for example diethyl ether, diisopropyl ether, t-butyl methyl ether, 1,2-dimethoxyethane, tetrahydrofuran, and 1,4-dioxane; carboxylic acids, for example formic acid and acetic acid; hydrocarbon solvents, for example pentane, hexane, toluene, and mixtures thereof; and mixtures thereof, particularly aqueous mixtures such as aqueous ethanol. Pure solvents, preferably at least analytical grade, and more preferably pharmaceutical grade, are preferably used. In a preferred embodiment of the processes of the invention, the products are so isolated. In the compounds of the invention having formulas selected from (Ia), (I-Ha), (IIa), (II-H), (II-Ha), (II-Hb), and (II-Hc) or salts thereof, and pharmaceutical compositions thereof, the compound having a formula selected from (Ia), (I-Ha), (IIa), (II-H), (II-Ha), (II-Hb), and (II-Hc), or salt thereof, is preferably in or prepared from a crystalline form, preferably prepared according to such a process.

The synthetic methods described above reflect a convergent synthesis strategy. Thus two components may be synthesized and elaborated separately prior to condensing or coupling the two compounds to form the target compounds. These convergent synthetic schemes allow for arrangement of the assembly steps of the backbone of the target compounds and derivatization of derivatizable functionalities to accommodate functional group sensitivity and/or to allow for functional groups or elements to be introduced either before or after the assembly of the backbone of the target compounds via the condensation or coupling reactions described.

It will be appreciated by one skilled in the art that certain aromatic substituents in compounds of the invention, intermediates used in the processes described above, or precursors thereto, may be introduced by employing aromatic substitution reactions to introduce or replace a substituent, or by using functional group transformations to modify an existing substituent, or a combination thereof. Such reactions may be affected either prior to or immediately following the processes mentioned above, and are included as part of the process aspect of the invention. The reagents and reaction conditions for such procedures are known in the art. Specific examples of procedures that may be employed include, but are not limited to: electrophilic functionalization of an aromatic ring, for example via nitration, halogenations, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforesaid processes, certain functional groups that would be sensitive to the reaction conditions may be protected by protecting groups. A protecting group is a derivative of a chemical functional group that would otherwise be incompatible with the conditions required to perform a particular reaction, which, after the reaction has been carried out, can be removed to regenerate the original functional group, by which the functional group is considered to have been "protected." Any chemical functionality that is a structural component of any of the reagents used to synthesize compounds of this invention may be optionally protected with a chemical protecting group if such a protecting group is useful in the synthesis of compounds of this invention. The person skilled in the art knows when protecting groups are indicated, symbolically or otherwise, how to select such groups, and processes that can be used for selectively introducing and selectively removing them, because methods, of selecting and using protecting groups have been extensively documented in the chemical literature. Techniques for selecting, incorporating, and removing chemical protecting groups may be found, for example, in THEODORA W. GREENE & PETER G. M. WUTS, PROTECTIVE GROUPS IN ORGANIC SYNTHESIS (John Wiley & Sons, Inc. 1999), the entire disclosure of which is incorporated by reference herein.

In addition to use of a protecting group, sensitive functional groups may be introduced as synthetic precursors to the functional group desired in the intermediate or final product. An example of this is an aromatic nitro ($-NO_2$) group. The aromatic nitro group does not undergo any of the nucleophilic reactions of an aromatic amino group. However, the nitro group can serve as the equivalent of a protected amino group because it is readily reduced to the amino group under mild conditions that are selective for the nitro group over most other functional groups.

It will be appreciated by one skilled in the art that the processes described are not the exclusive means by which compounds of the invention may be synthesized and that an extremely broad repertoire of synthetic organic reactions is available to be potentially employed in synthesizing compounds of the invention. The person skilled in the art knows how to select and implement appropriate synthetic routes. Suitable synthetic methods may be identified by reference to the literature, including reference sources such as: COMPREHENSIVE ORGANIC SYNTHESIS (B. M. Trost & I. Fleming eds., Pergamon Press 1991); COMPREHENSIVE ORGANIC FUNCTIONAL GROUP TRANSFORMATIONS (A. R. Katritzky et al., eds., Pergamon Press 1996); COMPREHENSIVE ORGANIC FUNCTIONAL GROUP TRANSFORMATIONS II (A. R. Katritzky & R. J. K. Taylor eds., 2d ed., Elsevier 2004); COMPREHENSIVE HETEROCYCLIC CHEMISTRY (A. R. Katritzky & C. W. Rees eds., Pergamon Press 1984); COMPREHENSIVE HETEROCYCLIC CHEMISTRY II (A. R. Katritzky et al., eds., Pergamon Press 1996); and J. MARCH, ADVANCED ORGANIC CHEMISTRY (4th ed., John Wiley & Sons 1992).

Salts of Compounds or Derivatives of the Invention

The compounds of the present invention may take the form of salts. The term "salts" embraces additional salts of free acids or free bases that are compounds of the invention. As used herein, the term "pharmaceutically acceptable salt" refers, unless otherwise stated, to salts that possess toxicity profiles within a range that affords utility in pharmaceutical applications.

Suitable pharmaceutically acceptable acid addition salts may be prepared from an inorganic acid or from an organic acid. Examples of inorganic acids include hydrochloric, hydrobromic, hydroiodic, nitric, carbonic, sulfuric, and phosphoric acids. Appropriate organic acids may be selected from: aliphatic; cycloaliphatic; aromatic; aralphatic; heterocyclic; carboxylic; and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid. In the present examples of compounds having formulas selected from (Ia), (I-Ha), (IIa), (II-H), (II-Ha), (II-Hb), and (II-Hc), compounds containing pyridine groups, or fused-ring pyridines, such as azaindoles, can be isolated as salts of inorganic acids or strong organic acids, e.g., hydrochloric acid or trifluoroacetic acid. In the present examples of compounds having formulas selected from (Ia), (I-Ha), (IIa), (II-H), (II-Ha), (II-Hb), and (II-Hc), i.e., compounds containing amino groups, said compounds can be isolated as salts of inorganic acids or strong acids, e.g., hydrochloric acid or trifluoroacetic acid.

Suitable pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine (tris(hydroxymethyl) aminomethane), and procaine.

All of these salts may be prepared by conventional means from the corresponding compound having a formula selected from (Ia), (I-Ha), (IIa), (II-H), (II-Ha), (II-Hb), and (II-Hc), by reacting, for example, the appropriate acid or base with the compound having a formula selected from (Ia), (I-Ha), (IIa), (II-H), (II-Ha), (II-Hb), and (II-Hc). Preferably the salts are in crystalline form, and preferably prepared by crystallization of the sale from a suitable solvent. The person skilled in the art will know how to prepare and select suitable salts forms, for example, as described in P. H. STAHL & C. G. WERMUTH, HANDBOOK OF PHARMACEUTICALS SALTS: PROPERTIES, SELECTION, AND USE (Wiley-VCH 2002), incorporated by reference herein.

Routes of Administration

The compounds may be administered by any route, including but not limited to oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of one or more NR, NAR, NRH, or NARH derivatives, including prodrugs, solvates, or salts thereof, in the body of the patient in a controlled formulation, with systemic or local release of the drug to occur at a later time. For example, the drug may be localized in a depot for controlled release to the circulation.

The methods described above may be further understood in connection with the following Examples. In each of the Examples, it is contemplated that NR, NAR, NRH, or NARH derivatives, including prodrugs or salts thereof, may be used.

Example 1

In one embodiment, one or more NR, NAR, NRH, or NARH derivatives, including prodrugs or salts thereof, may be used as a vehicle transdermal delivery of compounds and/or pharmaceutical products. In a preferred embodiment, the derivative is selected from NRH triacetate (2) and NARH triacetate (4a).

In another embodiment, one or more NR, NAR, NRH, or NARH derivatives, including prodrugs or salts thereof, may be used as follows: to improve the signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of barrier function, loss of skin recoil from deformation, discoloration, blotching, sallowness, hyperpigmentation, keratosis, hyperkeratinization, elastosis or collagen breakdown, and cellulite, or combinations thereof. In a preferred embodiment, the derivative is selected from NRH triacetate (2) and NARH triacetate (4a).

In another embodiment, one or more NR, NAR, NRH, or NARH derivatives, including prodrugs or salts thereof, may be used in a method for treating skin damage including rosacea, dermatitis, psoriasis, acne, and UV induced damage (including, for example, sunburn), or combinations thereof. In a preferred embodiment, the derivative is selected from NRH triacetate (2) and NARH triacetate (4a).

In another embodiment, one or more NR, NAR, NRH, or NARH derivatives, including prodrugs, solvates, or salts thereof, may be used to reduce the effects of oxidative stress to help prevent the signs of aging. In a preferred embodiment, the derivative is selected from NRH triacetate (2) and NARH triacetate (4a).

Example 2

In an embodiment, one or more NR, NAR, NRH, or NARH derivatives, including prodrugs, solvates, or salts thereof, may be used, optionally, in combination with pterostilbene. One useful dosage range for topical pterostilbene is from about 0.1% by weight to about 10% by weight, based on the total weight of the composition. Another suitable dosage range for topical pterostilbene is from about 1-2% by weight, based on the total weight of the composition. In a preferred embodiment, the derivative is selected from NRH triacetate (2) and NARH triacetate (4a). Useful dosage ranges for NRH triacetate (2) and NARH triacetate (4a) are about 0.1% to about 10% by weight, based on the total weight of the composition.

In this example, the NR-, NAR-, NRH-, or NARH-containing combination functions as a UV induced inflammatory modulator, impacting signs of aging and damage from, for example, UV/radiation including skin lightening, inflammation, and redness from sun burn.

Further, in another embodiment, the NR-, NAR-, NRH- or NARH-containing combination may be used in treating redness and inflammation associated with the following: acne, rosacea, psoriasis, radiation dermatosis, and wound healing. In a preferred embodiment, the derivative is selected from NRH triacetate (2) and NARH triacetate (4a).

In another embodiment, the NR-, NAR-, NRH-, or NARH-containing combination is used as follows: to improve the signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of barrier function, loss of skin recoil from deformation, discoloration, blotching, sallowness, hyperpigmentation, keratosis, hyperkeratinization, and elastosis or collagen breakdown, or combinations thereof. In a preferred embodiment, the derivative is selected from NRH triacetate (2) and NARH triacetate (4a).

In another embodiment, the NR-, NAR-, NRH-, or NARH-containing combination is used as follows: to repair DNA in skin, improve DNA repair in skin, and/or potentiate improved DNA-repair processes. In a preferred embodiment, the derivative is selected from NRH triacetate (2) and NARH triacetate (4a).

Example 3

NRH triacetate (2) and NARH triacetate (4a) treatment preventing oxidative damage in human skin cells.

A431 human epidermoid cells (ATCC # CRL1555) were grown in DMEM media (GIBCO) supplemented with 10% FBS and 1% PenStrep in T75 flasks based on culture recommendations. The media was replaced every two to three (2-3) days until >80% confluency was attained. The cells were trypsinized with 0.25% trypsin EDTA solution for 2-3 minutes until the cells were dislodged. The cells were sub-cultured in a ratio of 1:3 for further growth and scale-up for the assay. The cells were trypsinized and counted to a density of 5,000 or 15,000 cells and seeded in 100 µL media per well, in 96-well clear bottom black plates. The outer wells at the periphery of the plates were left unneeded and were instead filled with media to reduce the edge effect during incubation. The plates were incubated overnight in a humidified incubator at 37° C./5% $CO_2$ to confirm that the cells were attached. NRH triacetate compound (2) and NARH triacetate compound (4a) were added at indicated final assay concentrations in the media either under pre-treatment for 24 hours (without hydrogen peroxide) or along with 1 mM hydrogen peroxide for an incubation of 20 hours in a humidified incubator at 37° C./5% $CO_2$ either with media replenishment at 8 hours or under conditions using FBS. Each concentration was tested in 6 replicates. Appropriate controls: cells without compound and hydrogen peroxide (no cytotoxicity; negative control), cells without compound but in the presence of 1 mM hydrogen peroxide (positive control), wells with alamar blue alone (blank) were kept in each assay.

Post incubation the media from the plates was removed and replaced with 100 µL of 1× alamar blue solution in serum and phenol red free RPMI media. The plates were incubated at 37° C. for a further 1-4 hours, followed by reading at Ex/Em=560/590 nm on Flex Station3 plate reader (Molecular Devices). Detection method used: Cell Titer blue (Promega, Cat# G8080).

Cell viability was graphed and data was represented as percent cytotoxicity for 1 mM $H_2O_2$ under a given assay condition with respect to negative (untreated control) cells or percent cytoprotection in the presence of the test compound calculated with respect to positive (1 mM $H_2O_2$) control.

Figure 1:
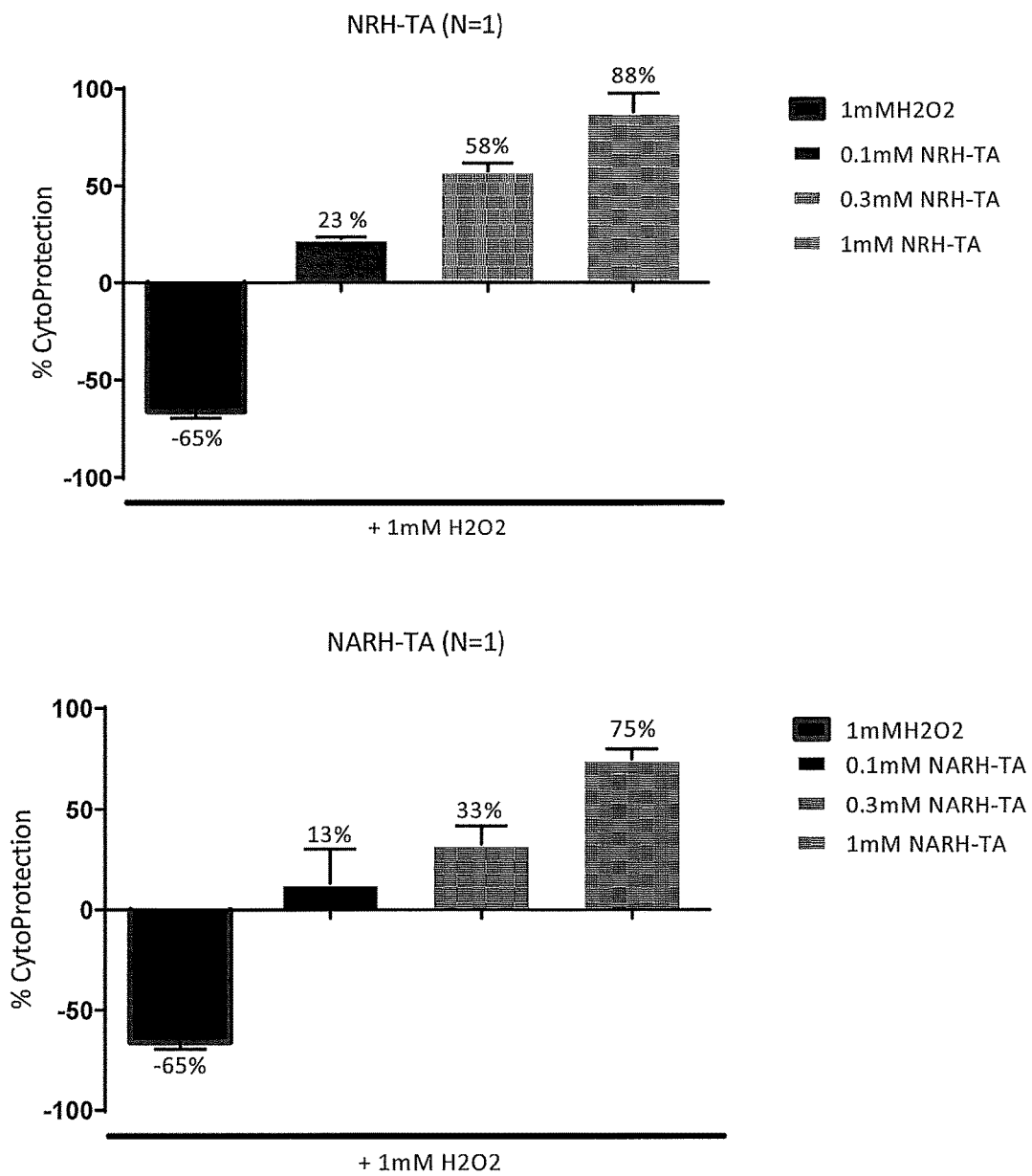

Trial A. Thus, as described above, NRH triacetate (2) and NARH triacetate (4a) were assayed for their ability to combat oxidative damage in human skin cells. A431 cells were treated with 1 mM hydrogen peroxide ($H_2O_2$) for 20 hours in the presence or absence of 0.1 mM, 0.3 mM, or 1 mM NRH triacetate (2) or NARH triacetate (4a). As shown in FIG. 1, all doses of NRH triacetate (2) and NARH triacetate (4a) were capable of mitigating oxidative damage to human skin cells. Further, clear dose-dependent cytoprotection was observed up to 88% cytoprotection for NRH triacetate (2) and 75% cytoprotection for NARH triacetate (4a), respectively, compared to positive controls.

Figure 2:
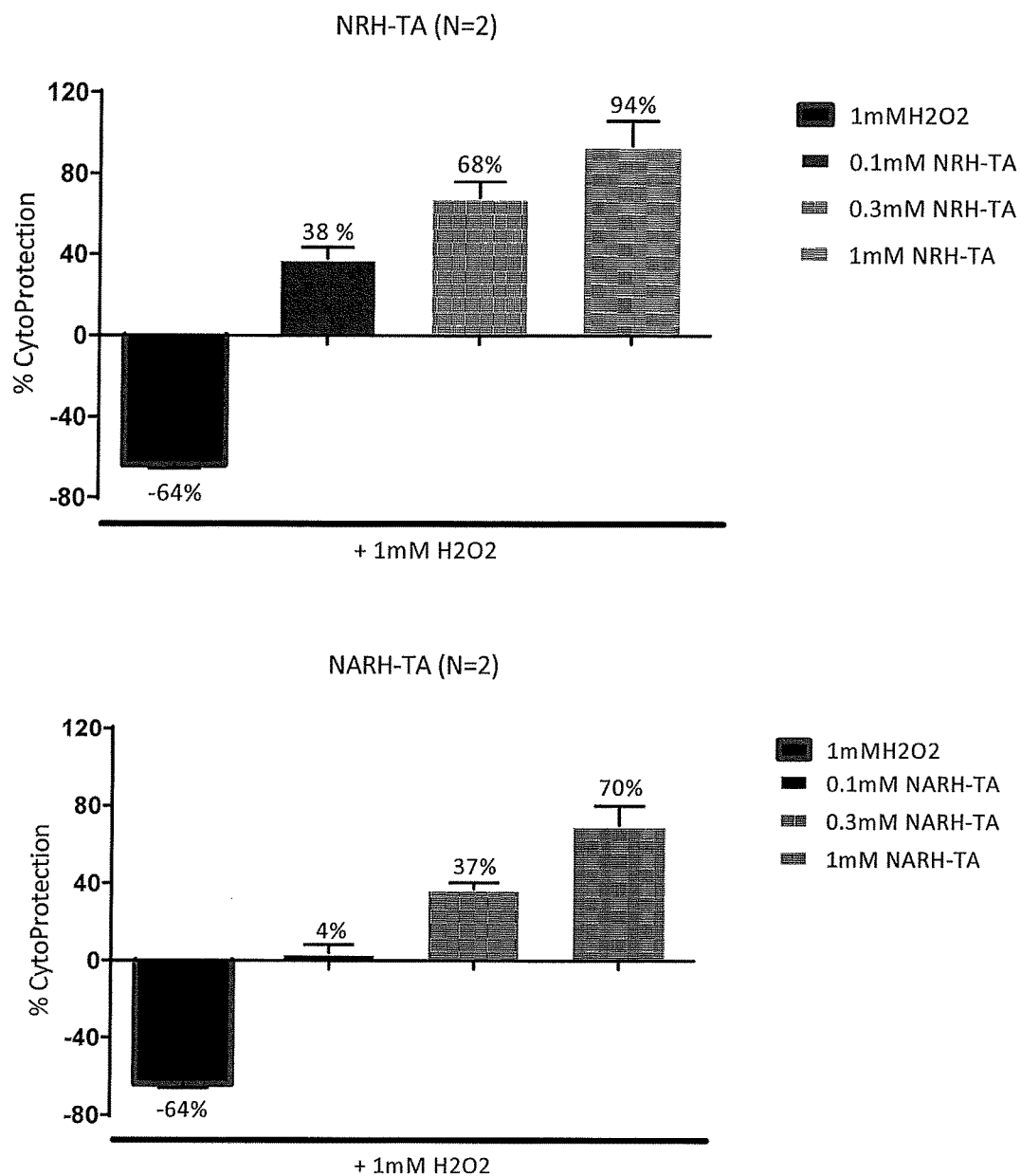
FIG. 2 depicts a replicate of the experiment of FIG. 1.

Trial B. The results of Trial A were replicated in a second, independent study as shown in FIG. 2. In this experiment, NRH triacetate (2) achieved 94% cytoprotection at 1 mM and NARH triacetate (4a) demonstrated 70% cytoprotection at 1 mM, respectively, compared to positive controls. Dose-dependent results were also observed in this experiment for both compounds.

Figure 3:
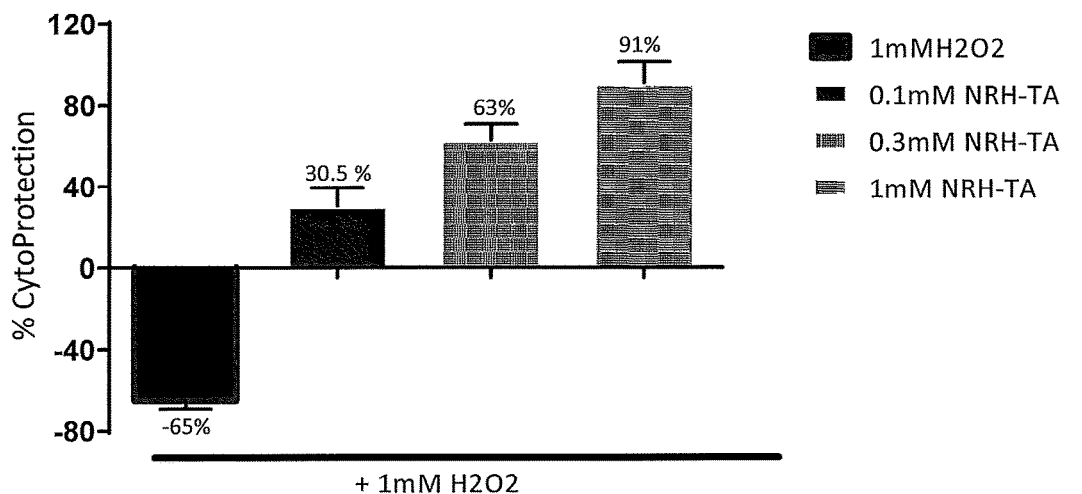
FIG. 3 depicts composite graphs of the experiments of FIGS. 1 and 2.
Figure 3:
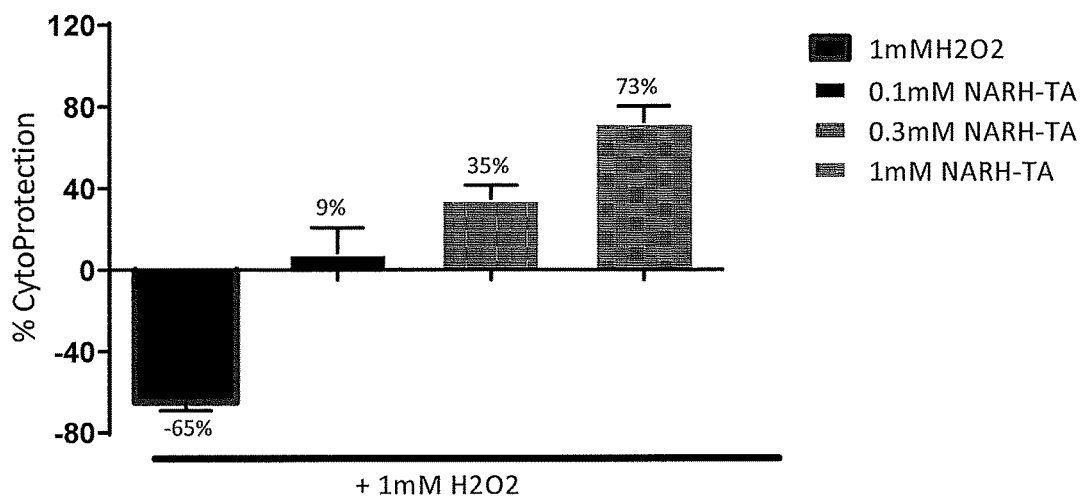

A composite graph is shown in FIG. 3 that includes both experiments together. Again a dose dependent effect was observed. These results clearly show that both NRH triacetate (2) and NARH triacetate (4a) can protect against oxidative damage in skin cells.

Example 4

NR Triacetate (1) and NAR Triacetate (3) Treatment Preventing Oxidative Damage in Human Skin Cells Compared to NARH (II-H), NRH (I-H), NAR (II), and NR (I)

A431 human epidermoid cells were maintained in DMEM supplemented with 10% FBS and 1% PenStrep, with a media change every 2-3 days until 80% confluency was attained. The cells were harvested using 0.25% trypsin EDTA solution and were seeded into 96-well clear bottom black plates counted to a density of 5,000 cells per well, and allowed to adhere overnight. The compounds, NR triacetate (1), NAR triacetate (3), NARH (II-Ha), NRH (I-H), NAR (II), and NR (I), were added at desired final assay concentrations under pre-treatment for 24 hours, without hydrogen peroxide, in a humidified incubator at 37° C./5% $CO_2$. After pre-treatment, hydrogen peroxide was added at final concentration of 1 mM along with the desired concentrations of test compounds, and incubated for 24 hours. Each concentration was tested in 3 replicates. Appropriate controls: cells without compound and hydrogen peroxide (no cytotoxicity; negative control), cells without compound but in the presence of 1 mM hydrogen peroxide (positive control), wells with alamar blue alone (blank) were kept in each assay.

Post incubation the media from the plates was removed and replaced with 100 µL of 1× alamar blue solution in PBS. The plates were incubated at 37° C. for a further 1-4 hours, followed by reading at Ex/Em=560/590 nm on Flex Station3 plate reader.

As shown in FIGS. 4-5, >40% cytoprotection was observed at 0.04 and 0.2 mM NRH (I-H), while less than 20% cytoprotective effect was observed in the presence of NARH (II-H) over oxidative damage caused by 1 mM $H_2O_2$. Higher concentrations of both NARH (II-H) and NRH (I-H) exhibited cytotoxicity.

As shown in FIGS. 6-7, approximately 40% cytoprotection was observed at 0.04 and 0.2 mM NAR (1), while a dose-dependent (>40%) cytoprotective effect was observed in the presence of NR (I) over oxidative damage caused by 1 mM $H_2O_2$. Cytotoxicity was observed at 5 mM NAR (II), while NR (I) did not exhibit any cytotoxicity.

As shown in FIGS. 8-9, dose-dependent cytoprotection was observed with NRTA (1) and NARTA (3) over oxidative damage caused by 1 mM $H_2O_2$. No cytotoxicity was observed in the presence of NRTA (1) and NARTA (3), whereas NARH (II-H) and NRH (I-H) were found to be cytotoxic at high concentrations (NRH (I-H) at 5 mM, 1 mM; NARH (II-H) at 5 mM, 1 mM, and 0.2 mM) amongst all test compounds on A431 cells.

TABLE 1

Cytotoxicity of Test Compounds on A431 Cells

| Test Sample | % Cytotoxicity (Concentration in mM) | | | |
|---|---|---|---|---|
| | 5 | 1 | 0.2 | 0.04 |
| NARH (II-Ha) | 96 | 26 | −7 | 6 |
| NRH (I-H) | 77 | 71 | 27 | −4 |
| NAR (II) | −8 | −7 | 1 | 0 |
| NR (I)* | 12 | 11 | 6 | 3 |
| NRTA (1)* | −7 | 10 | 19 | 18 |
| NARTA (3) | 22 | 12 | 8 | 9 |

*Administered as chloride salt

Example 5

A. Synthetic Preparation of Triacetyl Nicotinic Acid Riboside (Compound 3)

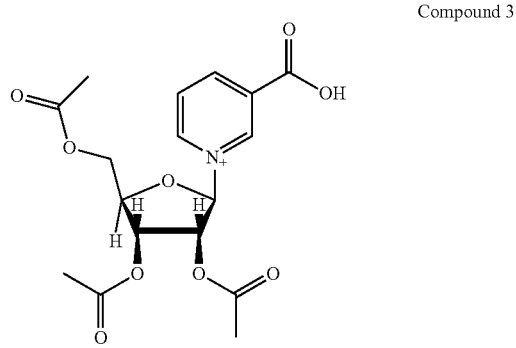

Compound 3

To a dry round-bottom flask with a condenser was added nicotinic acid (40.0 g, 0.32 mol, 1.0 eq.) followed by HMDS (203.3 mL, 0.97 mol, 3.0 eq.) and a catalytic amount of ammonium sulfate (approx. 30 mg). The sample was then heated to reflux under an atmosphere of nitrogen and left stirring for 24 hours. The solution was allowed to cool to room temperature and then HMDS was removed under reduced pressure to give trimethylsilyl pyridine-3-carboxylate (63.5 g, 0.32 mol) assuming quantitative yield and was used in the subsequent step without any further modification.

The trimethylsilyl pyridine-3-carboxylate (63.5 g, 324.9 mmol) was then solubilized in freshly distilled DCE (100 mL), followed by the single addition of tetraacetate riboside (108.6 g, 341.2 mmol, 1.05 eq.), and then TMSOTf (58.8 mL, 324.9 mmol, 1.0 eq.) was added in one portion. This solution as then heated to 40° C. and left stirring overnight under an atmosphere of N₂. Once the conversion was complete by ¹H-NMR analysis, the solution was concentrated under reduced pressure to provide a thick oil. The oil was then re-solubilized into dichloromethane (approx. 100 mL) and then water (approx. 200 mL) was added with rapid stirring. To the stirring biphasic solution, a saturated solution of NaHCO₃ was slowly added to maintain a constant pH >4.0. After the pH had stabilized, indicating complete hydrolysis of the NAR silyl ester, the pH of the solution was further adjusted to 6.0. The solution was then transferred to a separating funnel and was washed with dichloromethane (3×200 mL). The organic extracts where discarded and the aqueous layer was then freeze-dried to give an off-white solid. A 1.0-gram sample of the crude, was taken and solubilized in the minimal amount of dichloromethane and purified by silica gel column purification on a biotage system using an eluent of 40% MeOH in EtOAc to provide 400 mg of Compound 3 as a white crystalline solid.

$^1$H NMR (400 MHz, D$_2$O): δ ppm 9.28 (1H, s, Ar), 8.98 (1H, d, J=6.1 Hz, Ar), 8.83 (1H, d, J=7.8 Hz, Ar), 8.06 (1H, t, J=6.8 Hz, Ar), 6.46 (1H, d, J=3.7 Hz, β H-1), 5.46 (1H, t, J=4.7 Hz, H-3), 5.37 (1H, t, J=5.4 Hz, H-2), 4.80-4.77 (1H, m, H-4), 4.44-4.41 (2H, m, H-5), 2.05 (3H, s, OAc), 2.03 (3H, s, OAc), 1.99 (3H, s, OAc). $^{13}$C NMR (125 MHz, D$_2$O): δ ppm 176.7, 173.5, 172.5, 164.6 (3×O=C—CH₃, COOH), 148.4 (Ar), 143.7 (Ar), 141.7 (Ar), 133.0 (Ar), 128.8 (Ar), 97.4 (C-1), 82.3 (C-3), 76.6 (C-2), 69.7 (C-5), 62.8 (C-4), 20.3 (O=C—CH₃), 20.0 (O=C—CH₃), 19.9 (O=C—CH₃).

B. Synthetic Preparation of 1-(2',3',5'-triacetyl-beta-D-ribofuranosyl)-1,4-dihydronicotinic Acid (Compound 4a)

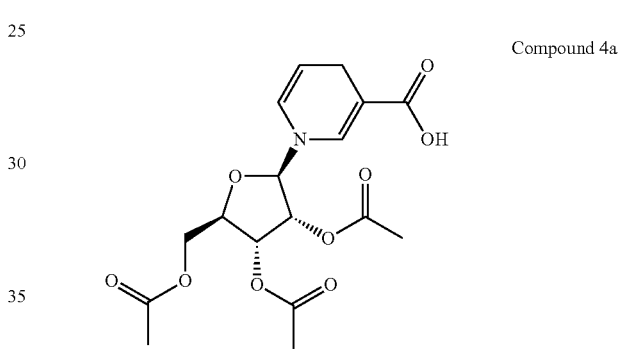

Compound 4a

NaHCO₃ (34.2 g, 407.1 mmol, 5.0 eq.) was dissolved in minimal H₂O followed by the addition of Na₂S₂O₄ (85%, 33.4 g, 191.6 mmol, 2.0 eq.). NAR triacetate triflate salt (43.4 g, 81.4 mmol, 1.0 eq.) was dissolved in minimal H₂O and added into the solution and stirred for 3 hours. Additional NaHCO₃ and dithionite (1:1 mol:mol) was added until saturation of the solution and a deep yellow color resulted. The mixture was extracted with EtOAc (3×500 mL) and the organic layer extracted with brine until the fluorine peak representing the triflate counterion was absent by $^{19}$F NMR. The organic layer was then dried over MgSO₄, filtered and concentrated under high vacuum to yield 19.00 g (61%) of Compound 4a as a yellow solid.

$^1$H NMR (400 MHz, MeOD): δ ppm 7.19 (d, J=1.5 Hz, 1H, N—HC=C—COOEt), 5.93 (dq, J=8.3, 1.6 Hz, 1H, N—HC=CH), 5.14 (dd, J=5.6, 2.6 Hz, 1H, H-3), 5.10 (dd, J=7.0, 5.8 Hz, 1H, H-2), 4.95 (d, J=7.0 Hz, 1H, H-1), 4.76 (dt, J=8.0, 3.5 Hz, 1H, N—HC=CH), 4.16-4.12 (m, 3H, H-4, H-5, H-5'), 2.90 (dd, J=3.0, 1.5 Hz, 2H, N—HC=CH—CH₂), 2.03 (s, 3H, OAc), 1.99 (s, 3H, OAc), 1.96 (s, 3H, OAc). $^{13}$C NMR (125 MHz, MeOD): δ ppm 172.2, 171.5, 171.5, 171.3 (3×O=C—CH₃, COOH), 140.0 (N—HC=C—COOH), 126.8 (N—HC=CH), 106.2 (N—HC=CH), 101.6 (N—HC=C—COOH), 94.2 (C-1), 80.5 (C-4), 72.3, 72.2 (C-2, C-3), 64.5 (C-5), 23.4 (N—HC=CH—CH₂), 20.8, 20.6, 20.4 (3×O=C—CH₃). HRMS (ES, M+H⁺) calculated for C₁₇H₂₂NO₉ 384.1295; found 384.1300.

C. Synthetic Preparation of 1-(beta-D-ribofuranosyl)-1,4-dihydronicotinic Acid (Compound II-Ha)

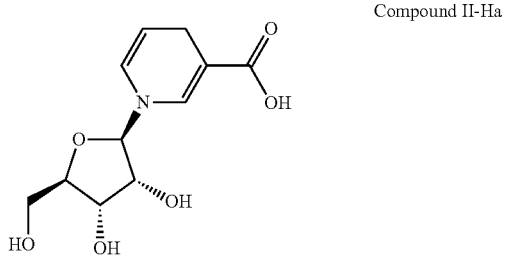 [SMILES: O=C(O)C1=CN([C@@H]2O[C@H](CO)[C@@H](O)[C@H]2O)C=CC1]

Compound II-Ha

A 25% solution of NaOMe in MeOH (1.35 mL, 23.8, mmol, 1.05 eq.) was added all in one portion to a solution of Compound 4a (8.68 g, 22.6 mmol, 1.0 eq.) in 100 mL MeOH at room temperature. After 30 minutes, the deprotection of Compound 4a was complete by $^1$H NMR. The solution was concentrated to afford Compound II-Ha sodium salt as an orange solid in quantitative yield.

$^1$H NMR (400 MHz, D$_2$O): δ ppm 6.86 (br s, 1 h, N—H$\underline{C}$=C—COOH), 5.91 (dq, J=8.3, 1.5 Hz, 1H, N—H$\underline{C}$=CH), 4.76 (dt, J=8.1, 3.5 Hz, 1H, N—HC=C$\underline{H}$), 4.74 (d, J=7.0 Hz, 1H, H-1), 4.05 (dd, J=6.9, 5.9 Hz, 1H, H-2), 3.97 (dd, J=5.5, 3.0 Hz, 1H, H-3), 3.82-3.77 (m, 1H, H-4), 3.60 (ABX, J$_{ab}$=12.5 Hz, J$_{ax}$=3.7 Hz, 1H, H-5), 3.55 (ABX, J$_{ab}$=12.5 Hz, J$_{bx}$=4.8 Hz, 1H, H-5'), 2.87 (br s, 2H, N—HC=CH—C$\underline{H}_2$). $^{13}$C NMR (125 MHz, D$_2$O): δ ppm 177.1 ($\underline{C}$OOH), 136.4 (N—H$\underline{C}$=C—COOH), 126.1 (N—H$\underline{C}$=CH), 106.1 (N—HC=$\underline{C}$—COOH), 104.8 (N—HC=$\underline{C}$H), 94.9 (C-1), 83.2 (C-4), 70.8 (C-2), 70.2 (C-3), 61.7 (C-5), 23.2 (N—HC=CH—$\underline{C}$H$_2$). HRMS (ES, M+Na$^+$) calculated for C$_{11}$H$_{15}$NO$_6$Na, 280.0797; found 280.0794.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments the values may range in value either above or below the stated value in a range of approximately ±5%; in other embodiments the values may range in value either above or below the stated value in a range of approximately ±2%; in other embodiments the values may range in value either above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:
1. A compound of formula (II-Hc), or a salt or solvate thereof:

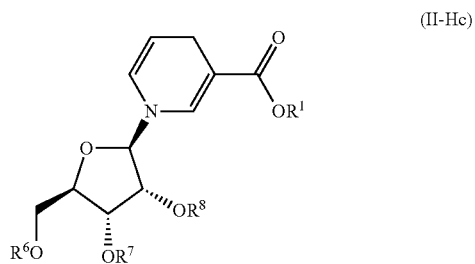

(II-Hc)

wherein R$^1$ is selected from hydrogen and (C$_1$-C$_4$)alkyl;
wherein R$^6$ is selected from the group consisting of hydrogen, —C(O)R', —C(O)OR', —C(O)NHR', substituted or unsubstituted (C$_1$-C$_8$)alkyl, substituted or unsubstituted (C$_3$-C$_8$)cycloalkyl, substituted or unsubstituted aryl, substituted or unsubstituted heteroaryl, and substituted or unsubstituted heterocycle;
R' is selected from the group consisting of hydrogen, —(C$_1$-C$_8$)alkyl, (C$_3$-C$_8$)cycloalkyl, aryl, heteroaryl, heterocycle, aryl(C$_1$-C$_4$)alkyl, and heterocycle(C$_1$-C$_4$)alkyl; and
R$^7$ and R$^8$ are independently selected from the group consisting of hydrogen, —C(O)R', —C(O)OR', —C(O)NHR', substituted or unsubstituted (C$_1$-C$_8$)alkyl, substituted or unsubstituted (C$_3$-C$_8$)cycloalkyl, substituted or unsubstituted aryl, substituted or unsubstituted heteroaryl, substituted or unsubstituted heterocycle, substituted or unsubstituted aryl(C$_1$-C$_4$)alkyl, and substituted or unsubstituted heterocycle(C$_1$-C$_4$)alkyl;
provided that R$^1$ is not ethyl;
provided that when R$^1$, R$^7$, and R$^8$ are simultaneously hydrogen, then R$^6$ is not C(O)-aryl;
provided that R$^1$, R$^6$, R$^7$, and R$^8$ are not all simultaneously hydrogen; and
provided that when R$^1$ is (C$_1$-C$_4$)alkyl, then R$^6$, R$^7$, and R$^8$ are not all simultaneously C(O)R', wherein R' is (C$_1$-C$_8$)alkyl.

2. A compound of claim 1 which is 1-(2',3',5'-triacetyl-beta-D-ribofuranosyl)-1,4-dihydronicotinic acid, or a salt or solvate thereof.

3. A cytoprotective method for treating skin damage in an individual comprising administering in need of such treatment a therapeutically effective amount of at least one compound of formula (I-Ha), or a salt or solvate thereof:

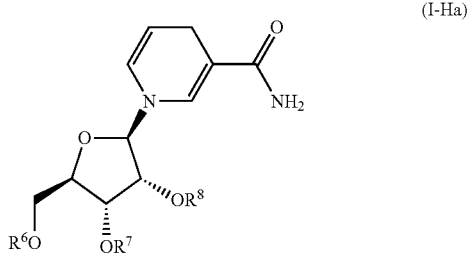

(I-Ha)

wherein R⁶ is selected from the group consisting of hydrogen, —C(O)R', —C(O)OR', —C(O)NHR', substituted or unsubstituted (C₁-C₈)alkyl, substituted or unsubstituted (C₃-C₈)cycloalkyl, substituted or unsubstituted aryl, substituted or unsubstituted heteroaryl, and substituted or unsubstituted heterocycle;

R' is selected from the group consisting of hydrogen, —(C₁-C₈)alkyl, (C₃-C₈)cycloalkyl, aryl, heteroaryl, heterocycle, aryl(C₁-C₄)alkyl, and heterocycle(C₁-C₄)alkyl;

R⁷ and R⁸ are independently selected from the group consisting of hydrogen, —C(O)R', —C(O)OR', —C(O)NHR', substituted or unsubstituted (C₁-C₈)alkyl, substituted or unsubstituted (C₃-C₈)cycloalkyl, substituted or unsubstituted aryl, substituted or unsubstituted heteroaryl, substituted or unsubstituted heterocycle, substituted or unsubstituted aryl(C₁-C₄)alkyl, and substituted or unsubstituted heterocycle(C₁-C₄)alkyl;

provided that in formula (I-Ha), when R⁶ is —C(O)R' or —C(O)OR', and R' is unsubstituted (C₁-C₈)alkyl or unsubstituted (C₃-C₈)cycloalkyl or unsubstituted aryl, then R⁷ and R⁸ are not simultaneously hydrogen or —C(O)R' or —C(O)OR'; or at least one compound of formula (II-Hc), or a salt or solvate thereof:

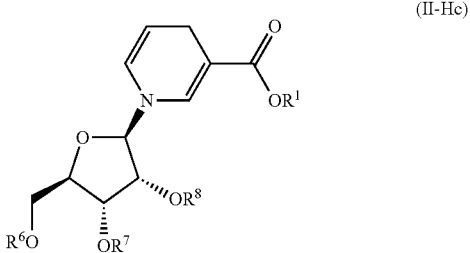

(II-Hc)

wherein R⁶, R⁷, and R⁸ are as defined above for the compounds of formula (I-Ha) and wherein R¹ is selected from hydrogen and (C₁-C₄)alkyl.

4. The cytoprotective method of claim 3, wherein the individual is a human.

5. The cytoprotective method of claim 3, wherein the at least one compound, or a salt or solvate thereof, is provided in a composition comprising a pharmaceutically acceptable carrier.

6. The cytoprotective method of claim 3, wherein the method of administration is selected from the group consisting of oral, topical, sublingual, buccal, ocular, pulmonary, rectal, parenteral, nasal, intravenous, intramuscular, intraarterial, intraperitoneal, intranasal, intravaginal, intravesical, intradermal, transdermal, and subcutaneous.

7. The cytoprotective method of claim 3, wherein skin damage is selected from the group consisting of oxidative damage, aging, superficial wrinkles, a coarse deep wrinkle, enlarged pores, age spots, photodamage, scaliness, flakiness, dryness, sagging in skin, puffiness in skin around an eye, puffiness in skin around a jowl, reduction of skin elasticity, reduction of skin firmness, reduction of skin tightness, reduction of barrier function, reduction of skin recoil from deformation, discoloration, blotching, sallowness, hyperpigmentation, keratosis, hyperkeratinization, elastosis, collagen breakdown, and combinations thereof.

8. The cytoprotective method of claim 3, wherein the at least one compound, or a salt or solvate thereof, is selected from the group consisting of: reduced nicotinic acid riboside (NARH), reduced nicotinamide riboside (NRH), and 1-(2',3',5'-triacetyl-beta-D-ribofuranosyl)-1,4-dihydronicotinic acid (NARH-TA).

9. The cytoprotective method of claim 3, wherein the at least one compound is a salt of 1-(2',3',5'-triacetyl-beta-D-ribofuranosyl)-1,4-dihydronicotinic acid (NARH-TA), the counterion of which is selected from the group consisting of sodium, potassium, lithium, magnesium, and calcium.

10. The cytoprotective method of claim 3, wherein the therapeutically effective amount of the at least one compound, or a salt or solvate thereof, for a total dose is in a range of about 0.1% by weight to about 50% by weight based on the total weight of the composition.

11. The cytoprotective method of claim 3, wherein the therapeutically effective amount of the at least one compound, or a salt or solvate thereof, for a total dose is in a range of about 0.1% by weight to about 10% by weight based on the total weight of the composition.

12. The cytoprotective method of claim 9, wherein skin cell viability is at least about 75%.

13. The cytoprotective method of claim 9, where skin cell viability is at least about 80%.

14. The cytoprotective method of claim 9, where skin cell viability is at least about 90%.

15. A cytoprotective method of treating skin damage in an individual comprising administering to the individual in need of such treatment a therapeutically effective amount of at least one compound of formula (Ia), or a salt or solvate thereof:

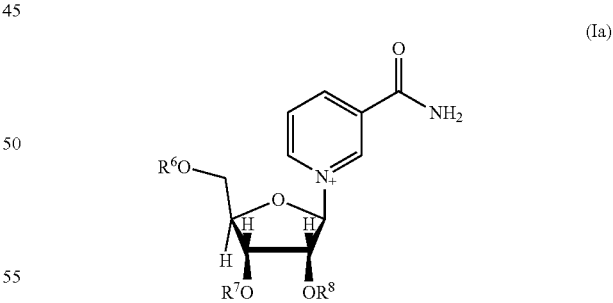

(Ia)

wherein R⁶ is selected from the group consisting of, —C(O)R', —C(O)OR', —C(O)NHR', substituted or unsubstituted (C₁-C₈)alkyl, substituted or unsubstituted (C₃-C₈)cycloalkyl, substituted or unsubstituted aryl, substituted or unsubstituted heteroaryl, and substituted or unsubstituted heterocycle;

R' is selected from the group consisting of hydrogen, —(C₁-C₈)alkyl, (C₃-C₈)cycloalkyl, aryl, heteroaryl, heterocycle, aryl(C₁-C₄)alkyl, and heterocycle(C₁-C₄)alkyl; and R⁷ and R⁸ are independently selected from the group consisting of hydrogen, —C(O)R', —C(O)OR', —C(O)NHR', substituted or unsubstituted (C₁-C₈)alkyl, substituted or unsubstituted (C₃-C₈)cycloalkyl, substituted or unsubstituted aryl, substituted or unsubstituted heteroaryl, substituted or unsubstituted heterocycle, substituted or unsubstituted aryl(C₁-C₄)alkyl, and substituted or unsubstituted heterocycle(C₁-C₄)alkyl;

provided that in formula (Ia), R⁶, R⁷, and R⁸ are not all simultaneously hydrogen;

provided that in formula (Ia), when R⁶ is —C(O)R' or —C(O)OR', and R' is unsubstituted (C₁-C₈)alkyl or unsubstituted (C₃-C₈)cycloalkyl or unsubstituted aryl, then R⁷ and R⁸ are not simultaneously hydrogen or —C(O)R' or —C(O)OR'; or at least one compound of formula (IIa), or a salt or solvate thereof:

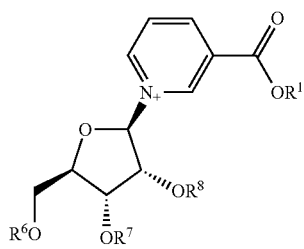

(IIa)

wherein R⁶, R⁷, and R⁸ are as defined above for the compounds of formula (Ia) and wherein R¹ is hydrogen.

16. The cytoprotective method of claim 15, wherein the individual is a human.

17. The cytoprotective method of claim 15, wherein the at least one compound, or a salt or solvate thereof, is provided in a composition comprising a pharmaceutically acceptable carrier.

18. The cytoprotective method of claim 15, wherein the method of administration is selected from the group consisting of oral, topical, sublingual, buccal, ocular, pulmonary, rectal, parenteral, nasal, intravenous, intramuscular, intraarterial, intraperitoneal, intranasal, intravaginal, intravesical, intradermal, transdermal, and subcutaneous.

19. The cytoprotective method of claim 15, wherein skin damage is selected from the group consisting of oxidative damage, aging, superficial wrinkles, a coarse deep wrinkle, enlarged pores, age spots, photodamage, scaliness, flakiness, dryness, sagging in skin, puffiness in skin around an eye, puffiness in skin around a jowl, reduction of skin elasticity, reduction of skin firmness, reduction of skin tightness, reduction of barrier function, reduction of skin recoil from deformation, discoloration, blotching, sallowness, hyperpigmentation, keratosis, hyperkeratinization, elastosis, collagen breakdown, and combinations thereof.

20. The cytoprotective method of claim 15, wherein the at least one compound, or a salt or solvate thereof, is selected from the group consisting of nicotinic acid riboside (NAR) and 1-(2',3',5'-triacetyl-beta-D-ribofuranosyl)-nicotinic acid (NARTA).

21. The cytoprotective method of claim 15, wherein the at least one compound of formula (IIa) is a salt of NAR or 1-(2',3',5'-triacetyl-beta-D-ribofuranosyl)-nicotinic acid (NARTA), the counterion of which is selected from the group consisting of: internal salt, sodium, potassium, lithium, magnesium, calcium, fluoride, chloride, bromide, iodide, formate, acetate, ascorbate, benzoate, carbonate, citrate, carbamate, gluconate, lactate, methyl bromide, methyl sulfate, nitrate, phosphate, diphosphate, succinate, sulfate, trifluoromethanesulfonate, and trifluoroacetate.

22. The cytoprotective method of claim 15, wherein the therapeutically effective amount of the at least one compound, or a salt or solvate thereof, for a total dose is in a range of about 0.01% by weight to about 50% by weight based on the total weight of the composition.

23. The cytoprotective method of claim 15, wherein the therapeutically effective amount of the at least one compound, or a salt or solvate thereof, for a total dose is in a range of about 0.1% by weight to about 10% by weight based on the total weight of the composition.

24. The cytoprotective method of claim 21, wherein skin cell viability is at least about 50%.

25. The cytoprotective method of claim 21, wherein skin cell viability is at least about 60%.

26. The cytoprotective method of claim 21, wherein skin cell viability is at least about 75%.

* * * * *

UNITED STATES PATENT AND TRADEMARK OFFICE
CERTIFICATE OF CORRECTION

PATENT NO. : 10,280,190 B2
APPLICATION NO. : 15/072121
DATED : May 7, 2019
INVENTOR(S) : Ryan Dellinger et al.

Page 1 of 1

It is certified that error appears in the above-identified patent and that said Letters Patent is hereby corrected as shown below:

On the Title Page

(73) Assignees: ChromaDex, Inc. Irvine, CA (US); The Queen's University of Belfast, Belfast (IE)
Delete "(IE)" and insert -- , Northern Ireland (GB) --.

In the Claims

In Claim 3, Column 28, Line 65, after the term "administering" insert the phrase -- to the individual --.

In Claim 8, Column 30, Line 16, delete ")" after " 3',5'".

Signed and Sealed this
Thirty-first Day of December, 2019

Andrei Iancu
*Director of the United States Patent and Trademark Office*